(12) United States Patent
Li et al.

(10) Patent No.: US 10,252,987 B2
(45) Date of Patent: Apr. 9, 2019

(54) TYPE OF ANTIVIRAL COMPOUND

(71) Applicant: Institute of Medicinal Biotechnology, Chinese Academy of Medical Sciences, Beijing (CN)

(72) Inventors: Yanping Li, Beijing (CN); Zhuorong Li, Beijing (CN); Zonggen Peng, Beijing (CN); Jianrui Li, Beijing (CN); Xinbei Jiang, Beijing (CN); Jinhua Chen, Beijin (CN); Jiandong Jiang, Beijing (CN)

(73) Assignee: Institute of Medicinal Biotechnology, Chinese Academy of Medical Sciences, Beijing (CN)

( * ) Notice: Subject to any disclaimer, the term of this patent is extended or adjusted under 35 U.S.C. 154(b) by 0 days.

(21) Appl. No.: 15/743,297

(22) PCT Filed: Aug. 17, 2016

(86) PCT No.: PCT/CN2016/000459
§ 371 (c)(1),
(2) Date: Jan. 10, 2018

(87) PCT Pub. No.: WO2017/028472
PCT Pub. Date: Feb. 23, 2017

(65) Prior Publication Data
US 2018/0208549 A1    Jul. 26, 2018

(30) Foreign Application Priority Data

Aug. 18, 2015  (CN) .......................... 2015 1 0509150

(51) Int. Cl.
| | | |
|---|---|---|
| *A61P 31/16* | (2006.01) | |
| *C07C 255/50* | (2006.01) | |
| *C07C 255/58* | (2006.01) | |
| *C07D 241/04* | (2006.01) | |
| *C07D 213/85* | (2006.01) | |
| *C07D 295/13* | (2006.01) | |
| *C07D 401/04* | (2006.01) | |
| *C07D 211/56* | (2006.01) | |
| *C07D 295/155* | (2006.01) | |

(52) U.S. Cl.
CPC ............ *C07C 255/50* (2013.01); *A61P 31/16* (2018.01); *C07C 255/58* (2013.01); *C07D 211/56* (2013.01); *C07D 213/85* (2013.01); *C07D 241/04* (2013.01); *C07D 295/13* (2013.01); *C07D 295/155* (2013.01); *C07D 401/04* (2013.01)

(58) Field of Classification Search
CPC ....... A61K 31/44; A61K 31/495; A61P 31/16; C07C 255/50; C07C 255/58; C07D 211/56; C07D 213/85; C07D 241/04; C07D 295/13; C07D 295/155; C07D 401/04
See application file for complete search history.

(56) References Cited

FOREIGN PATENT DOCUMENTS

WO    WO 2004/060308    * 7/2004

OTHER PUBLICATIONS

Written Opinion and International Search Report for PCT/CN2016/000459, dated Oct. 28, 2016; 16 pages.

* cited by examiner

*Primary Examiner* — Erich A Leeser
(74) *Attorney, Agent, or Firm* — Rankin Hill & Clark LLP

(57) ABSTRACT

Provided are a new aromatic cyanogen compound and a preparation method thereof. The present invention also relates to the use of such compound in antiviral drugs, in particular the use thereof in anti-HCV drugs.

23 Claims, No Drawings

TYPE OF ANTIVIRAL COMPOUND

TECHNICAL FIELD

The present invention relates to a class of novel substituted aryl cyanides and a preparation method thereof; and also involves the use of the compounds in the manufacture of antiviral drugs, wherein the virus refers to DNA viruses such as herpes viruses, hepatotropic viruses, adenoviruses, or nipple tumor virus; and RNA viruses, such as mumps viruses, influenza viruses, corona viruses, retroviruses, enterovirus or flavivirus; in particular involves the use of the compounds in the manufacture of drugs against HCV viruses.

BACKGROUND TECHNIQUE

Viral diseases are the most common infectious diseases, and have become global public health problems due to their features of highly infectivity and high variability. The targets of the existing antiviral drugs are mostly viral enzymes. Viral enzyme inhibitors drugs have advantages such as explicit targets, high specificity, and strong efficacy, but also apparent shortages of narrow antiviral spectrum, and problem of drug resistance leaded by the tends of the high variability of the viruses. The emerging of the new virus variants and unknown viruses make existing antiviral drugs, which have frequent problems of drug resistance, powerless. Therefore, the development of new antiviral drugs is imminent. Hepatitis C virus (HCV) infected about 200 million people in the entire world, wherein there are about 40 million HCV carriers in China. HCV is highly infectious. Once infected by HCV, it is difficult to spontaneously clear the viruses. 80% of those infected will become chronic hepatitis C (CHC). If no antiviral treatment is properly and timely received, 20-30% of patients with CHC will develop cirrhosis 20-30 years after the infection, and epidemiological studies have shown that chronic HCV infection is closely associated with primary liver cancer. There is no effective vaccine to prevent this infection. The combination of pegylated interferon α (PEG-IFN-α) and ribavirin (RBV) is current standard therapy for the treatment of chronic HCV infection, but this standard therapy has defects of significant side effects of toxicity and a long treatment course, so its clinical application has some limitations. In recent years, the rapid development of biology leads to a breakthrough understanding for people in terms of HCV infection and replication. Pharmaceutical companies developed a variety of HCV-specific antiviral drugs which act directly on the virus (DAAs). Recently, a new target treatment regimen without interferon has been proposed in the field of anti-HCV drug research. The new target treatment is similar to HIV cocktail therapy, and is formed by the combination of HCV inhibitor drugs with multiple action mechanisms, and ultimately treatment without interferon formed by the combination of a variety of small molecule inhibitors is promising. The ideal treatment regimen can block viral replication in many processes simultaneously, and help delaying drug resistance, but still needs research discoveries on novel HCV inhibitors with different mechanism of action as a basis.

The inventors found and confirmed that a group of benzamide compounds with broad spectrum inhibition of viral activity during the early screening study of antiviral drugs with host cell factor APOBEC3G as targets. Such compounds also significantly inhibit HCV replication, but have poor metabolic stability, and low bioavailability. When conducting structural optimization studies, the inventors discovered and confirmed that a new class of substituted aryl cyanides had better inhibitory activity on HCV replication and pharmaceutical properties had been improved significantly. Furthermore, the compounds of the present invention may play a broad-spectrum antiviral role on the basis of the new cellular mechanisms. The compounds of the invention and its role are not reported by relevant literature domestically and abroad to date.

SUMMARY

The main object of the present invention is to screen a new class of antiviral compounds and pharmaceutically acceptable salts thereof by structure-activity studies of substituted aryl cyanides, and the compounds not only have significant antiviral activity, but also have advantages such as low toxicity, good pharmaceutical properties.

To achieve the above object, the present invention provides a series compounds having the structure represented by the following formula I or a pharmaceutically acceptable salt thereof:

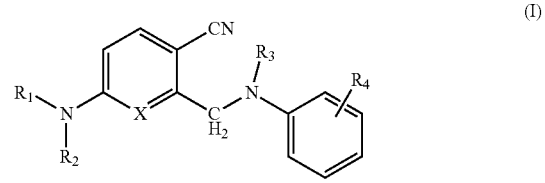

wherein $R_1$ is amino C1-C4 alkyl wherein the amino is substituted by $R_8$ and/or $R_9$, $R_8$ and $R_9$ are H or C1-C4 alkyl, or form a six-membered ring together with the nitrogen atom to which they are bonded, the six-membered ring is selected from piperidine or piperazine, $R_2$ is H or C1-C4 alkyl; or $R_1$ and $R_2$ form a six-membered ring together with the nitrogen atom to which they are bonded, the said six-membered ring is selected from substituted or unsubstituted piperazine or piperidine, wherein the piperazine or piperidine is substituted by C1-C4 alkyl, C1-C4 alkoxy, C2-C4 alkenyl, phenyl, amino or halogen;

$R_3$ is H or C1-C4 alkyl; $R_4$ is H or one or more substitutents selected from a group consisting of C1-C4 alkyl, C5-C6 cycloalkyl, C1-C4 alkoxy, phenoxy, phenylthio and halogen at any available position(s) of the phenyl ring; X is N or C.

In a preferred embodiment of the invention, there is provided a compound having the structure as shown in the following formula II or a pharmaceutically acceptable salt thereof:

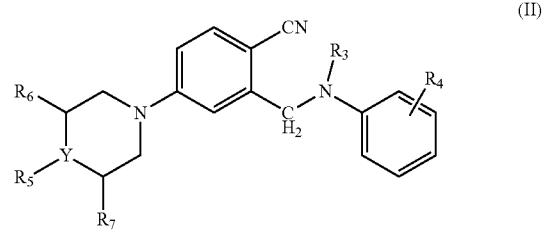

wherein $R_3$ is H or C1-C4 alkyl, $R_4$ is H or one or more substituents selected from a group consisting of straight-chain or branched-chain C1-C4 alkyl, C5-C6 cycloalkyl, C1-C4 alkoxy, phenoxy, phenylthio and halogen at any available position(s) on the phenyl ring, $R_5$ is H, C1-C4 alkyl, C2-C4 alkenyl, or phenyl, $R_6$ and $R_7$ are H, C1-C4 alkyl or amino respectively or simultaneously, Y is N or C; preferably, $R_3$ is H, methyl, ethyl or propyl, $R_4$ is H or methyl, ethyl, isopropyl, tert-butyl, cyclopentyl, cyclohexyl, methoxy, ethoxy, phenoxy, phenylthio, chloro or bromo at para position of the phenyl ring, $R_5$ is H, methyl, ethyl, propyl, allyl or phenyl, $R_6$ and $R_7$ are H, methyl, ethyl, propyl, or amino simultaneously or separately, Y is N or C.

In another preferred embodiment of the invention, there is provided a compound having the structure represented by the following Formula III or a pharmaceutically acceptable salt thereof:

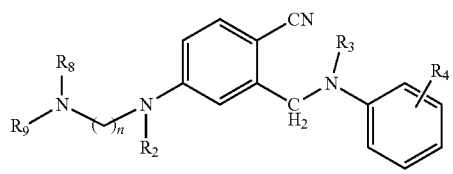

(III)

wherein, $R_2$ is H or C1-C4 alkyl, $R_8$ and $R_9$ are H or C1-C4 alkyl, or, form a six-membered ring together with the nitrogen atom to which they are bonded, the said six-membered ring is selected from piperazine or piperidine, $R_3$ is H or C1-C4 alkyl, $R_4$ is H or one or more substituents selected from a group consisting of straight-chain or branched-chain C1-C4 alkyl, C5-C6 cycloalkyl, C1-C4 alkoxy group, phenoxy, phenylthio and halogen at any available position(s) on the phenyl ring, n is an integer from 1 to 4; preferably, $R_2$ is H, methyl or ethyl, $R_8$ and $R_9$ are H, methyl or ethyl, or form a piperidine ring together with the nitrogen atom to which they are bonded, $R_3$ is H, methyl, ethyl or propyl, $R_4$ is H or methyl, ethyl, isopropyl, tert-butyl, methoxy, ethoxy, chloro or bromo at para position of the phenyl ring, and n is 1, 2, or 3.

In a further preferred embodiment of the present invention, there is provided a compound having the structure represented by the following Formula IV or a pharmaceutically acceptable salt thereof:

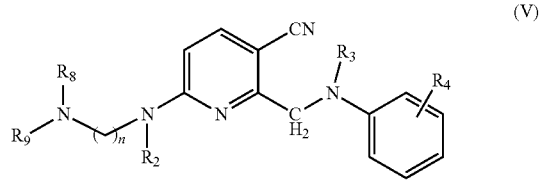

(IV)

wherein $R_3$ is H or C1-C4 alkyl, $R_4$ is H or one or more substituents selected from a group consisting of straight-chain or branched-chain C1-C4 alkyl, C5-C6 cycloalkyl, C1-C4 alkoxy, phenoxy, phenylthio and halogen at any available position(s) on the phenyl ring, $R_5$ is H, C1-C4 alkyl, C2-C4 alkenyl, or phenyl, $R_6$ and $R_7$ are H, C1-C4 alkyl or amino respectively or simultaneously, Y is N or C; preferably, $R_3$ is H, methyl, ethyl or propyl, $R_4$ is H or methyl, ethyl, isopropyl, tert-butyl, cyclopentyl, cyclohexyl, methoxy, ethoxy, phenoxy, phenylthio, chloro or bromo at para position of the phenyl ring, $R_5$ is H, methyl, ethyl, propyl, allyl or phenyl, $R_6$ and $R_7$ are H, methyl, ethyl, propyl, or amino simultaneously or separately, Y is N or C.

In a further preferred embodiment of the present invention, there is provided a compound having the structure represented by the following Formula V or a pharmaceutically acceptable salt thereof:

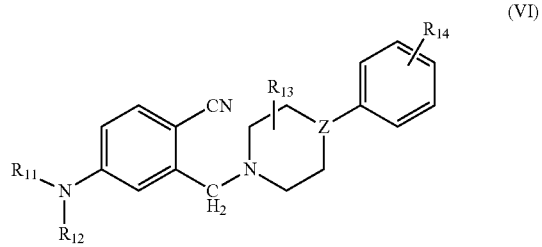

(V)

wherein $R_2$ is H or C1-C4 alkyl, $R_8$ and $R_9$ are H or C1-C4 alkyl, or, form a six-membered ring together with the nitrogen atom to which they are bonded, the said six-membered ring is selected from piperazine or piperidine, $R_3$ is H or C1-C4 alkyl, $R_4$ is H or one or more substituents selected from a group consisting of straight-chain or branched-chain C1-C4 alkyl, C5-C6 cycloalkyl, C1-C4 alkoxy group, phenoxy, phenylthio and halogen at any available position(s) on the phenyl ring, n is an integer from 1 to 4; preferably, $R_2$ is H, methyl or ethyl, $R_8$ and $R_9$ are H, methyl or ethyl, or form a piperidine ring together with the nitrogen atom to which they are bonded, $R_3$ is H, methyl, ethyl or propyl, $R_4$ is H or methyl, ethyl, isopropyl, tert-butyl, methoxy, ethoxy, chloro or bromo at para or meta position of the phenyl ring, and n is 1, 2 or 3.

In order to achieve the above object, the present invention also provides a series having the structure represented by the following formula VI compound or a pharmaceutically acceptable salt thereof:

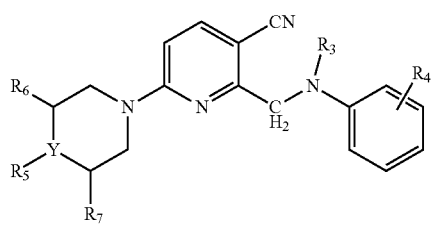

(VI)

wherein $R_{11}$ is amino C1-C4 alkyl wherein the amino is substituted by $R_{18}$ and/or $R_{19}$, $R_{18}$ and $R_{19}$ are H or C1-C4 alkyl, or, form a saturated five- or six-membered ring together with the nitrogen atom to which they are bonded, the said saturated five- or six-membered ring is selected from a group consisting of pyrrolidine, morpholine, piperazine and piperidine, $R_{12}$ is H or C1-C4 alkyl; or $R_{11}$ is

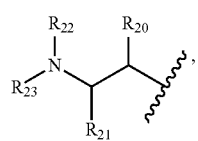

$R_{23}$ is H or C1-C4 alkyl, $R_{22}$ and $R_{21}$ are H or C1-C4 alkyl, or $R_{22}$ and $R_{21}$ form a saturated five- or six-membered ring together with the nitrogen atom to which they are bonded, the said saturated five- or six-membered ring is selected from a group consisting of pyrrolidine, morpholine, piperazine and piperidine, $R_{20}$ is H or C1-C4 alkyl, $R_{12}$ is H or C1-C4 alkyl;

or $R_{11}$ and $R_{12}$ form a saturated five- or six-membered ring together with the nitrogen atom to which they are bonded, the said saturated five- or six-membered ring selected from a group consisting of pyrrolidine, morpholine, piperazine and piperidine, wherein the saturated five- or six-membered ring are substituted by substituent(s) selected from a group consisting of C1-C4 alkyl, C1-C4 alkoxy, C2-C4 alkenyl, phenyl, amino, methylamino, dimethylamino or halogen;

$R_{13}$ is H or C1-C4 alkyl; $R_{14}$ is H or one or more substituents selected from a group consisting of C1-C4 alkyl, C5-C6 cycloalkyl, C1-C4 alkoxy, phenoxy, methylthio, phenylthio, amino, methylamino, dimethylamino, hydroxy, trifluoromethyl, trifluoromethoxy, cyano or halogen at any available position(s) of the phenyl ring, preferably the above substituent(s) which is para-monosubstituted or are disubstituted at any available positions of the phenyl ring;

Z is N or C.

In a preferred embodiment of the invention, there is provided a compound having the structure represented by the following formula VII or a pharmaceutically acceptable salt thereof:

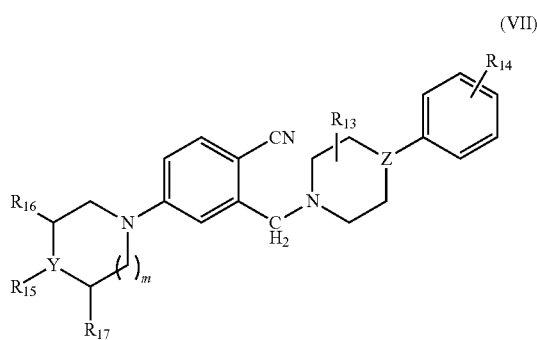

(VII)

wherein $R_{13}$ is H or C1-C4 alkyl, $R_{14}$ is H or one or more substituents selected from a group consisting of straight-chain or branched-chain C1-C4 alkyl, C5-C6 cycloalkyl, C1-C4 alkoxy, phenoxy, phenylthio, methylthio, amino, methylamino, dimethylamino, hydroxyl, trifluoromethyl, trifluoromethoxy, cyano and halogen at any available position(s) of the phenyl ring, $R_{15}$ is H, C1-C4 alkyl, C2-C4 alkenyl, phenyl, amino, methylamino or dimethylamino, $R_{16}$ and $R_{17}$ are H, C1-C4 alkyl or amino respectively or simultaneously, Y is N or C, and $R_{15}$ are not amino, methylamino or dimethylamino simultaneously when Y is N; m is 0 or 1; and Y is C when m is 0;

Preferably, $R_{13}$ is H, methyl, ethyl or propyl, $R_{14}$ is the H or the substitute(s) selected from a group consisting of methyl, ethyl, isopropyl, tert-butyl, cyclopentyl, cyclohexyl, methoxy, ethoxy, phenoxy, phenylthio, methylthio, amino, methylamino, dimethylamino, hydroxyl, trifluoromethyl, trifluoromethoxy, cyano, chloro and bromo which is para-monosubstituted or are disubstituted at any available positions of the phenyl ring, $R_{15}$ is H, methyl, ethyl, propyl, allyl or phenyl, $R_{16}$ and $R_{17}$ are H, methyl, ethyl, propyl or amino simultaneously or respectively; Y is N or C; $R_{15}$ are not amino, methylamino or dimethylamino simultaneously when Y is N; m is 0 or 1; and Y is C when m is 0.

In another preferred embodiment of the invention, there is provided a compound having the structure shown in the following formula VIII or a pharmaceutically acceptable salt thereof:

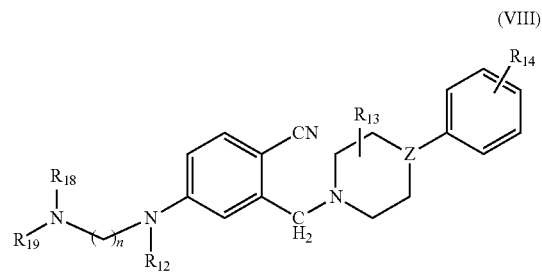

(VIII)

wherein, $R_{12}$ is H or C1-C4 alkyl, $R_{18}$ and $R_{19}$ are H or C1-C4 alkyl, or, form a saturated five- or six-membered ring together with the nitrogen atom to which they are bonded, the said saturated five- or six-membered ring is selected from pyrrolidine, morpholine, piperazine and piperidine, $R_{13}$ is H or C1-C4 alkyl, $R_{14}$ is H or one or more substituents selected from a group consisting of straight-chain or branched-chain C1-C4 alkyl, C5-C6 cycloalkyl, C1-C4 alkoxy, phenoxy, phenylthio, trifluoromethyl, trifluoromethoxy and halogen at any available position(s) of the phenyl ring, n is an integer of 1-4, Z is C or N; Preferably, $R_{12}$ is H, methyl or ethyl, $R_{18}$, $R_{19}$ is H, methyl or ethyl, or form a pyrrolidine or piperidine ring together with the nitrogen atom to which they are bonded to, $R_{13}$ is H, methyl, ethyl or propyl, $R_{14}$ is H or substitute(s) selected from a group consisting of methyl, ethyl, isopropyl, tert-butyl, methoxy, ethoxy, trifluoromethyl, trifluoromethoxy, chloro and bromo which is para-monosubstituted or are disubstituted at any available positions of the phenyl ring, n is 1, 2 or 3, Z is N or C.

In a further preferred embodiment of the present invention, there is provided a compound having the structure represented by the following formula IX or a pharmaceutically acceptable salt thereof:

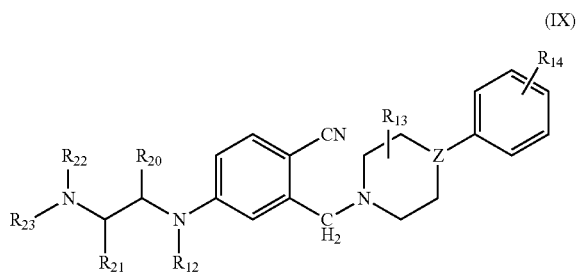

(IX)

wherein, $R_{23}$ is H or C1-C4 alkyl, $R_{22}$ and $R_{21}$ are H or C1-C4 alkyl, or $R_{22}$ and $R_{21}$ form a saturated five- or six-membered ring together with the nitrogen atom to which they are bonded, the said saturated five- or six-membered ring selected from pyrrolidine, morpholine, piperazine and piperidine, $R_{20}$ is H or C1-C4 alkyl, $R_{12}$ is H or C1-C4 alkyl, $R_{13}$ is H or C1-C4 alkyl, $R_{14}$ is H, or one or more substitutes selected from a group consisting of straight-chain or branched-chain C1-C4 alkyl, C5-C6 cycloalkyl, C1-C4 alkoxy, phenoxy, phenylthio and halogen at any available position(s) of the phenyl ring, Z is N or C;

Preferably, $R_{23}$ is H, methyl or ethyl, $R_{22}$ and $R_{21}$ are H, methyl or ethyl, or $R_{22}$, $R_{21}$ form pyrrolidine or piperazine ring together with the nitrogen atom to which they are bonded, $R_{20}$ is H, methyl or ethyl, $R_{12}$ is H, methyl or ethyl, $R_{13}$ is H, methyl, ethyl or propyl, $R_{14}$ is H or the substitute(s) selected from a group consisting of methyl, ethyl, isopropyl, tert-butyl, methoxy, ethoxy, chloro and bromo which is para-monosubstituted or are disubstituted at any available positions of the phenyl ring Z is N or C.

Regarding to the Above Definition:

"Substituents" involved in substitution or "substituted" may be, but not limited to, halogen, alkoxy, hydroxyl, alkyl, amino, alkyl amino, Aminoalkyl, alkenyl, phenyl. For example, "substituted piperazine" may be, but not limited to: piperazine substituted by halogen, alkoxy, hydroxyl, alkyl, amino, alkenyl, phenyl and substituted amino and the like at various positions of the piperazine. As another example, "substituted phenyl ring" may be, but not limited to: phenyl ring substituted by one substituent selected from a group consisting of alkyl, alkoxy, hydroxyl, amino, phenoxy, phenylthio, halogen and the like or phenyl ring substituted by two substituents selected from a group consisting of alkyl, alkoxy, hydroxyl, amino, phenoxy, phenylthio, halogen and the like at ortho or meta position.

"Alkyl" may be, but not limited to straight or branched chain alkyl with number of carbon atoms of 1-6, for example, methyl, ethyl, isopropyl, n-propyl, n-butyl, isobutyl, sec-butyl, tert-butyl, n-pentyl, isopentyl, n-hexyl, isohexyl and the like. C1-C4 lower alkyl is more preferable.

"Alkoxy" may be, but not limited to alkoxy with number of carbon atoms of 1 to 6, e.g., methoxy, ethoxy, isopropoxy, n-propoxy, n-butoxy, isobutoxy, sec-butoxy, tert-butoxy, n-pentyloxy, iso-pentoxy, n-hexyloxy, isohexyloxy. C1-C4 lower alkoxy is more preferable.

"Alkenyl" may be, but not limited to alkenyl with number of carbon atoms of 2 to 4, e.g., vinyl, propenyl, allyl, 1-butenyl, 2-butenyl, isobutenyl. Allyl is more preferable.

"Halo" or "halogen" may be fluoro, chloro, bromo or iodo. Chloro or bromo is more preferable.

"Aminoalkyl" may be, but not limited to alkyl with number of carbon atoms of 1-6 substituted by amino, e.g., aminomethyl, aminoethyl, aminoisopropyl, amino n-propyl, amino n-butyl, amino isobutyl, amino sec-butyl, amino tert-butyl, amino n-pentyl, amino isopentyl, amino n-hexyl, amino isohexyl and the like. Amino C1-C4 alkyl is more preferable.

"Amino", "Aminoalkyl" and "dialkylamino" respectively refer to —$NH_2$, —NHR and —$NR_2$, and R is an alkyl as defined above. Two alkyls connected to the nitrogen atom in dialkyl moiety may be the same or different.

Another object of the present invention is to provide a synthesis method of the compounds shown in the formula I, in which 2-methyl-4-fluorobenzonitrile or 6-fluoro-2-methyl-3-cyanopyridine (A) is a raw material. The method comprises following steps: a) obtaining intermediate compound (B) which methyl at position 2 is substituted by bromo via bromination by NBS, b) reacting the bromosubstituted intermediate then with the corresponding substituted aniline, using sodium ethoxide or potassium carbonate as acid binding agent to obtain the corresponding intermediate compound (C) of benzonitrile or cyanopyridine substituted by substituted phenylaminomethyl, c) finally, condensing the corresponding nitrogen-containing compound to remove HF (condensing the intermediate compound (C) with the corresponding nitrogen-containing compound to remove HF), thereby obtaining the desired product (compound of formula I, wherein $R_1$, $R_2$, $R_3$, $R_4$, X is defined as above) in the presence of a base such as potassium carbonate or triethylamine in a polar solvent such as DMF, butanol or DMSO.

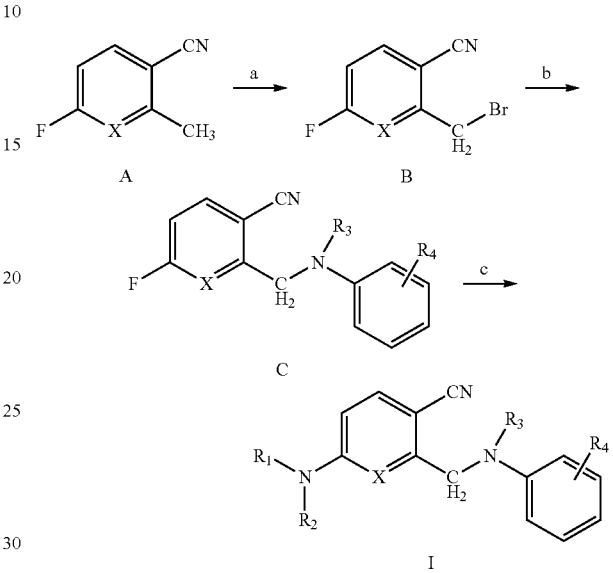

Another object of the present invention is to provide a synthesis method of a compound having the structure shown in formula VI, which is similar to the synthesis method of the compound of general formula I, except that in the reaction step b) aryl-substituted piperazine or piperidine is used to replace substituted aniline used in the synthesis of the compound of general formula I, the remaining steps are the same as those in the synthetic method of the compound of formula I, to obtain the desired product (compound of formula VI, wherein, $R_{11}$, $R_{12}$, $R_{13}$, $R_{14}$, Z is defined as above);

particularly, with 2-methyl-4-fluorobenzonitrile (A) as starting material, a) obtaining intermediate compound (B) with methyl at position 2 monosubstituted by bromo via bromination by NBS, b) reacting the bromosubstituted intermediate then with the corresponding piperazine or piperidine substituted by aryl group, using sodium ethoxide or potassium carbonate as acid binding agent to obtain the corresponding intermediate compound (C), c) finally, condensing the intermediate compound (C) with the corresponding nitrogen-containing compound to remove HF, thereby obtaining the desired product (compound of formula VI) in the presence of a base such as potassium carbonate or triethylamine in a polar solvent such as DMF, butanol or DMSO

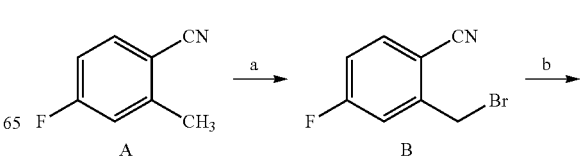

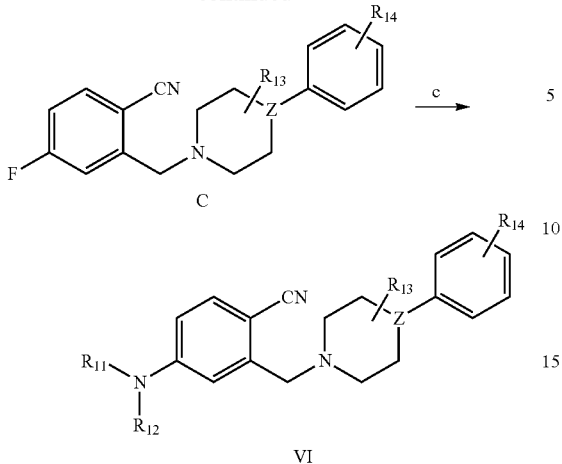

Further, another object of the present invention is to provide the compounds as mentioned above for use in antiviral drugs, especially in the anti-hepatitis virus drugs, especially anti-HCV drugs. The compounds as mentioned above are useful in prophylaxis and/or treatment of viral diseases, wherein the viral diseases are caused by DNA viruses, such as herpes viruses, hepatotropic viruses, adenoviruses, or papilloma viruses; or RNA viruses, such as mumps viruses, influenza viruses, corona viruses, retroviruses, enterovirus or flaviviruses, or hepatitis C viruses (HCV). Further, the compounds as mentioned above can be used in manufacturing a medicament, wherein the medicament is useful in prophylaxis and/or treatment of viral diseases, wherein the viral diseases are caused by DNA viruses, such as herpes viruses, hepatotropic viruses, adenoviruses, or papilloma viruses; or RNA viruses, such as mumps viruses, influenza viruses, corona viruses, retroviruses, enterovirus or flaviviruses, or hepatitis C viruses (HCV). The present invention also provide a method for prophylaxis and/or treatment of viral diseases, wherein the viral diseases are caused by DNA viruses, such as herpes viruses, hepatotropic viruses, adenoviruses, or papilloma viruses; or RNA viruses, such as mumps viruses, influenza viruses, corona viruses, retroviruses, enterovirus or flaviviruses, or hepatitis C viruses (HCV), and the method comprises administering therapeutically effective amount of the compound as mentioned above to a patient in need thereof.

The assay results of anti-HCV activity of the compound synthesized according to the present invention in cell culture are shown in Table 1, wherein the molecular weight is calculated by ChemBioDraw 12.0 software from the molecular structure of each compound.

TABLE 1 anti-HCV activity of the compounds

| No. | molecular weight | Chemical name | percent inhibition (%) |
|---|---|---|---|
| 1 | 306 | 4-(piperazin-1-yl)-2-((p-methylphenylamino)methyl)benzonitrile | 97 |
| 2 | 322 | 4-(piperazin-1-yl)-2-(p-methoxyphenylamino)methylbenzonitrile | 89 |
| 3 | 320 | 4-(4-methylpiperazin-1-yl)-2-(p-methylphenylamino)methylbenzonitrile | 92 |
| 4 | 306 | 4-(4-methylpiperazin-1-yl)-2-(phenylamino)methylbenzonitrile | 82 |
| 5 | 320 | 4-(3-methylpiperazin-1-yl)-2-(p-methylphenylamino)methylbenzonitrile | 88 |
| 6 | 320 | 4-(3-aminopiperidin-1-yl)-2-(p-methylphenylamino)methylbenzonitrile | 68 |
| 7 | 292 | 4-(piperazin-1-yl)-2-(phenylamino)methylbenzonitrile | 82 |
| 8 | 340 | 4-(4-methylpiperazin-1-yl)-2-(p-chlorophenylamino)methylbenzonitrile | 91 |
| 9 | 326 | 4-(piperazin-1-yl)-2-(p-chlorophenylamino)methylbenzonitrile | 92 |
| 10 | 336 | 4-(4-methylpiperazin-1-yl)-2-(p-methoxyphenylamino)methylbenzonitrile | 90 |
| 11 | 388 | 4-(4-methylpiperazin-1-yl)-2-(p-cyclohexylphenylamino)methylbenzonitrile | 97 |
| 12 | 362 | 4-(4-methylpiperazin-1-yl)-2-(p-tert-butylphenylamino)methylbenzonitrile | 92 |
| 13 | 334 | 4-(4-methylpiperazin-1-yl)-2-(p-ethylphenylamino)methylbenzonitrile | 87 |
| 14 | 334 | 4-(4-methylpiperazin-1-yl)-2-((p-methylphenyl)(methyl)amino)methylbenzonitrile | 97 |
| 15 | 383 | 4-(4-methylpiperazin-1-yl)-2-((p-chlorophenyl)(propyl)amino)methylbenzonitrile | 88 |
| 16 | 350 | 4-(4-methylpiperazin-1-yl)-2-((p-methoxyphenyl)(methyl)amino)methylbenzonitrile | 84 |
| 17 | 404 | 4-(4-methylpiperazin-1-yl)-2-((p-tert-butylphenyl)(propyl)amino)methylbenzonitrile | 96 |
| 18 | 334 | 4-(4-propylpiperazin-1-yl)-2-(phenylamino)methylbenzonitrile | 75 |
| 19 | 402 | 4-(4-allylpiperazin-1-yl)-2-((p-tert-butylphenyl)(methyl)amino)methylbenzonitrile | 86 |
| 20 | 412 | 4-(4-phenylpiperazin-1-yl)-2-((p-methoxyphenyl)(methyl)amino)methylbenzonitrile | 70 |
| 21 | 348 | 4-(4-methylpiperazin-1-yl)-2-(p-isopropylphenylamino)methylbenzonitrile | 90 |
| 22 | 440 | 4-(4-propylpiperazin-1-yl)-2-((p-phenoxyphenyl)(methyl)amino)methylbenzonitrile | 86 |
| 23 | 442 | 4-(4-propylpiperazin-1-yl)-2-(p-(phenylthio)phenylamino)methylbenzonitrile | 78 |
| 24 | 374 | 4-(4-methylpiperazin-1-yl)-2-(p-cyclopentylphenylamino)methylbenzonitrile | 94 |
| 25 | 364 | 4-(3,5-dimethylpiperazin-1-yl)-2-((p-methoxyphenyl)(methyl)amino)methylbenzonitrile | 75 |
| 26 | 322 | 4-(N,N-dimethyl-1,3-propanediamin-1-yl)-2-(p-methylphenylamino)methylbenzonitrile | 79 |
| 27 | 308 | 4-(N,N-dimethyl-1,3-propanediamin-1-yl)-2-(phenylamino)methylbenzonitrile | 78 |
| 28 | 348 | 4-((2-(piperidin-1-yl)ethyl)amino)-2-(p-methylphenylamino)methylbenzonitrile | 65 |
| 29 | 342 | 4-(N,N-dimethyl-1,3-propanediamin-1-yl)-2-(p-chlorophenylamino)methylbenzonitrile | 80 |
| 30 | 338 | 4-(N,N-dimethyl-1,3-ethylenediamin-1-yl)-2-(p-methoxyphenylamino)methylbenzonitrile | 49 |
| 31 | 350 | 2-((4-methoxyphenyl)amino)methyl-4-(piperidin-1-ylmethyl)aminobenzonitrile | 61 |
| 32 | 336 | 2-((4-tert-butylphenyl)amino)methyl-4-((N,N-dimethylamino)methyl)aminobenzonitrile | 73 |
| 33 | 364 | 2-((4-tert-butylphenyl)(methyl)amino)methyl-4-(((dimethylamino)methyl)(methyl)amino)benzonitrile | 89 |
| 34 | 445 | 2-(((4-cyclopentylphenyl)propylamino)methyl)-6-(2-(piperidin-1-yl)ethyl)amino-3-cyanopyridine | 76 |
| 35 | 375 | 6-(4-methylpiperazin-1-yl)-2-((4-cyclopentylphenylamino)methyl)-3-cyanopyridine | 80 |
| 36 | 337 | 2-((4-methoxyphenyl)amino)methyl-6-(4-methylpiperazin-1-yl)-3-cyanopyridine | 75 |

TABLE 1-continued anti-HCV activity of the compounds

| No. | molecular weight | Chemical name | percent inhibition (%) |
|---|---|---|---|
| 37 | 321 | 2-((4-methylphenyl)amino)methyl-6-(4-methylpiperazin-1-yl)-3-cyanopyridine | 72 |
| 38 | 338 | 6-((2-(dimethylamino)ethyl)(methyl)amino)-2-((4-methoxyphenyl)amino)methyl-3-cyanopyridine | 70 |
| 39 | 368 | 6-(((2-(dimethylamino)ethyl)(methyl)amino)-2-((3,5-dimethoxyphenyl)amino)methyl-3-cyanopyridine | 75 |
| 40 | 322 | 6-((2-(dimethylamino)ethyl)(methyl)amino)-2-((3-methylphenyl)amino)methyl-3-cyanopyridine | 84 |
| 41 | 471 | 2-((4-(phenylthio)phenyl)(ethyl)amino)methyl-6-(4-propylpiperazin-1-yl)-3-cyanopyridine | 57 |
| 42 | 385 | 2-(((4-bromophenyl)amino)methyl)-4-(4-methylpiperazin-1-yl)benzonitrile | 87 |
| VI-1 | 393 | 4-((N',N'-dimethyl-1,2-ethylenediamin-1-yl)-2-(4-(4-methoxyphenyl)piperazin-1-yl)methylbenzonitrile | 99 |
| VI-2 | 420 | 4-(((piperidin-1-yl)methyl)amino)-2-(4-(4-methoxyphenyl)piperazin-1-yl)methylbenzonitrile | 62 |
| VI-3 | 406 | 4-((4-methyl)piperazin-1-yl)-2-(4-(4-methoxyphenyl)piperazin-1-yl)methylbenzonitrile | 91 |
| VI-4 | 390 | 4-((4-methyl)piperazin-1-yl)-2-(4-(4-methylphenyl)piperazin-1-yl)methylbenzonitrile | 98 |
| VI-5 | 392 | 4-(piperazin-1-yl)-2-(4-(4-methoxyphenyl)piperazin-1-yl)methylbenzonitrile | 79 |
| VI-6 | 376 | 4-(piperazin-1-yl)-2-(4-(4-methylphenyl)piperazin-1-yl)methylbenzonitrile | 88 |
| VI-7 | 390 | 4-(3-aminopiperidin-1-yl)-2-((4-(4-methylphenyl)piperazin-1-yl)methyl)benzonitrile | 71 |
| VI-8 | 361 | 4-(piperazin-1-yl)-2-(4-(4-phenyl)piperazin-1-yl)methylbenzonitrile | 82 |
| VI-9 | 410 | 4-(4-methylpiperazin-1-yl)-2-(4-(4-chlorophenyl)piperazin-1-yl)methylbenzonitrile | 92 |
| VI-10 | 396 | 4-(piperazin-1-yl)-2-(4-(4-chlorophenyl)piperazin-1-yl)methylbenzonitrile | 73 |
| VI-11 | 404 | 4-(4-methylpiperazin-1-yl)-2-(4-(3,4-dimethylphenyl)piperazin-1-yl)methylbenzonitrile | 80 |
| VI-12 | 458 | 4-(4-methylpiperazin-1-yl)-2-(4-(4-cyclohexylphenyl)piperazin-1-yl)methylbenzonitrile | 86 |
| VI-13 | 432 | 4-(4-methylpiperazin-1-yl)-2-(4-(4-tert-butylphenyl)piperazin-1-yl)methylbenzonitrile | 90 |
| VI-14 | 404 | 4-(4-methylpiperazin-1-yl)-2-(4-(4-ethylphenyl)piperazin-1-yl)methylbenzonitrile | 88 |
| VI-15 | 410 | 4-(piperazin-1-yl)-2-(4-(3-methyl4-chlorophenyl)piperazin-1-yl)methylbenzonitrile | 95 |
| VI-16 | 418 | 4-(4-methylpiperazin-1-yl)-2-(4-(4-isopropylphenyl)piperazin-1-yl)methylbenzonitrile | 68 |
| VI-17 | 422 | 4-(4-methylpiperazin-1-yl)-2-(4-(4-(methylthio)phenyl)piperazin-1-yl)methylbenzonitrile | 70 |
| VI-18 | 454 | 4-(4-methylpiperazin-1-yl)-2-(4-(4-bromophenyl)piperazin-1-yl)methylbenzonitrile | 86 |
| VI-19 | 392 | 4-(4-methylpiperazin-1-yl)-2-(4-(4-hydroxylphenyl)piperazin-1-yl)methylbenzonitrile | 67 |
| VI-20 | 405 | 4-(4-methylpiperazin-1-yl)-2-(4-(4-methylaminophenyl)piperazin-1-yl)methylbenzonitrile | 78 |
| VI-21 | 419 | 4-(4-methylpiperazin-1-yl)-2-(4-(4-dimethylaminophenyl)piperazin-1-yl)methylbenzonitrile | 65 |
| VI-22 | 447 | 4-((2-(dimethylamino)ethyl)(methyl)amino)-2-(4-(4-(pyrrolidin-1-yl)phenyl)piperazin-1-yl)methylbenzonitrile | 83 |
| VI-23 | 414 | 4-(4-methylpiperazin-1-yl)-2-(4-(3-methyl-4-cyanophenyl)piperidin-1-yl)methylbenzonitrile | 77 |
| VI-24 | 444 | 4-(4-methylpiperazin-1-yl)-2-(4-(4-cyclopentylphenyl)piperazin-1-yl)methylbenzonitrile | 59 |
| VI-25 | 420 | 4-(2,6-dimethylpiperazin-1-yl)-2-(4-p-methoxyphenyl)-1-yl)methylbenzonitrile | 67 |
| VI-26 | 392 | 4-(N',N'-dimethyl-1,3-propanediamin-1-yl)-2-(4-p-methylphenylpiperazin-1-yl)methylbenzonitrile | 58 |
| VI-27 | 378 | 4-(N',N'-dimethyl-1,3-propanediamin-1-yl)-2-(4-phenylpiperazin-1-yl)methylbenzonitrile | 60 |
| VI-28 | 431 | 4-(N',N'-dimethyl-1,2-ethylenediamin-1-yl)-2-(4-p-trifluoromethylphenyl-piperazin-1-yl)methylbenzonitrile | 79 |
| VI-29 | 412 | 4-(N',N'-dimethyl-1,3-propanediamin-1-yl)-2-(4-p-chlorophenylpiperazin-1-yl)methylbenzonitrile | 80 |
| VI-30 | 394 | 4-(N',N'-dimethyl-1,2-ethylenediamin-1-yl)-2-(4-p-methoxyphenylpiperazin-1-yl)methylbenzonitrile | 66 |
| VI-31 | 408 | 4-(N,N',N'-trimethyl-1,2-ethylenediamin-1-yl)-2-(4-p-methoxyphenylpiperazin-1-yl)methylbenzonitrile | 91 |
| VI-32 | 474 | 4-(N,N',N'-trimethyl1,3-propanediamin-1-yl)-2-(4-p-cyclohexylphenylpiperazin-1-yl)methylbenzonitrile | 80 |
| VI-33 | 406 | 2-(4-(4-tert-butylphenyl)piperazin-1-yl)methyl-4-((N,N-dimethylamino)methyl)amino-benzonitrile | 90 |
| VI-34 | 454 | 2-(4-(4-bromophenyl)piperazin-1-yl)methyl-4-(4-methylpiperazin-1-yl)benzonitrile | 91 |
| VI-35 | 412 | 4-(N,N',N'-trimethyl-1,2-ethylenediamin-1-yl)-2-(4-p-chlorophenylpiperazin-1-yl)methylbenzonitrile | 99 |

TABLE 1-continued anti-HCV activity of the compounds

| No. | molecular weight | Chemical name | percent inhibition (%) |
|---|---|---|---|
| VI-36 | 418 | 4-((methyl)((piperidin-1-yl)-methyl)amino)-2-(4-p-methylphenylpiperazin-1-yl)methylbenzonitrile | 91 |
| VI-37 | 404 | 4-((methyl)((pyrrolidin-1-yl)-methyl)amino)-2-(4-p-methylphenylpiperazin-1-yl)methylbenzonitrile | 87 |
| VI-38 | 431 | 4-(4-methylpiperazin-1-yl)-2-(4-(4-tert-butylphenyl)piperidin-1-yl)methylbenzonitrile | 80 |
| VI-39 | 411 | 4-(N,N',N'-trimethyl-1,2-ethylenediamin-1-yl)-2-(4-p-chlorophenylpiperidin-1-yl)methylbenzonitrile | 88 |
| VI-40 | 433 | 4-((methyl)((morpholine-4-yl)ethyl))amino-2-(4-p-methylphenylpiperidin-1-yl)methylbenzonitrile | 65 |
| VI-41 | 433 | 4-((methyl)((pyrrolidin-1-yl)ethyl))amino-2-(4-p-methoxyphenylpiperidin-1-yl)methylbenzonitrile | 72 |
| VI-42 | 417 | 4-((methyl)((1-ethylpyrrolidin-2-yl)methyl))amino-2-(4-phenylpiperidin-1-yl)methylbenzonitrile | 80 |
| VI-43 | 432 | 4-((ethyl)((pyrrolidin-1-yl)ethyl))amino-2-(4-p-methylphenylpiperazin-1-yl)methylbenzonitrile | 84 |
| VI-44 | 424 | 4-((3-dimethylamino)pyrrolidin-1-yl)-2-(4-p-chlorophenylpiperazin-1-yl)methylbenzonitrile | 89 |
| VI-45 | 438 | 4-(N,N',N'-trimethyl-1,2-ethylenediamin-1-yl)-2-(3,4-dimethoxyphenylpiperazin-1-yl)methylbenzonitrile | 92 |
| VI-46 | 434 | 4-(1-(pyrrolidin-1-yl)propyl-2-yl)amino-2-(4-p-methoxyphenylpiperazin-1-yl)methylbenzonitrile | 95 |
| VI-47 | 462 | 4-(N,N',N'-trimethyl-1,2-ethylenediamin-1-yl)-2-(4-trifluoromethoxyphenylpiperazin-1-yl)methylbenzonitrile | 93 |

The present invention also provides an anti-viral pharmaceutical composition comprising a therapeutically effective amount of the compound having the general formula I, II, III, IV, V or a compound of formula VI, VII, VIII, IX or a pharmaceutically acceptable salt thereof, and containing one or more pharmaceutically acceptable pharmaceutical auxiliary material, adjuvants or excipients. The pharmaceutically acceptable salts refer to the product from salt forming reaction of a compound as mentioned above with an acid, including inorganic acid salts such as hydrochloride, hydrobromide or sulfate and the like; organic acid salts such as acetate, lactate, succinate, fumarate, maleate, citrate, benzoate, methanesulfonate, or 4-methylbenzoate salt.

The compound of formula I, II, III, IV, V or a compound of formula VI, VII, VIII, IX or a pharmaceutically acceptable salt thereof is used as an active ingredient, and present in an amount of 0.1% to 99.5% by weight of the pharmaceutical composition. Preferably, the pharmaceutical composition contains 0.5%-99.5% by weight of the active ingredient.

Further, the present invention provides a use of pharmaceutical composition in the manufacture of a medicament against viral infections. Since the compound of the present invention may play a broad-spectrum role against viruses on the basis of a new type of cellular mechanisms, wherein the viruses refer to DNA viruses, such as herpes viruses, hepatotropic viruses, adenoviruses, or papilloma viruses; and RNA viruses, such as mumps viruses, influenza viruses, corona viruses, retroviruses, enterovirus or flaviviruses. Preferably, the viruses mean hepatitis C viruses. The pharmaceutical compositions are useful in the prophylaxis and/or treatment of viral diseases, wherein the viral diseases are caused by DNA viruses, RNA virus, or hepatitis C virus. Further, the pharmaceutical compositions are useful in manufacturing a medicament, wherein the medicament is useful in prophylaxis and/or treatment of viral diseases, wherein the viral diseases are caused by DNA viruses, RNA virus, or hepatitis C virus. The present invention also provides a method for prophylaxis and/or treatment of viral diseases, wherein the viral diseases are caused by DNA viruses, RNA virus, or hepatitis C virus, and the method comprises administering therapically effective amount of the pharmaceutical compositions.

DETAILED DESCRIPTION

The present invention will be described in further detail by reference to the following specific examples, but the present invention is not limited to the following specific examples.

Example 1

Synthesis of Intermediate Compound 2-(p-methylphenylamino) methyl-4-fluoro-benzonitrile (1.1)

1.35 g 2-methyl-4-fluorobenzonitrile (10 mmol) was dissolved in 20 mL of carbon tetrachloride, and 0.25 g of p-toluene sulfonic acid (0.015 mmol) and 2.15 g N-bromo succinimide (NBS) (12 mmol) was added. The reaction was completed after heating for 4 hours, and then cooled to room temperature, filtered, and 20 mL saturated ammonium chloride solution was added and layers were obtained. The organic layer was washed with water and saturated sodium chloride aqueous solution (20 mL×3) successively to clarification, dried over anhydrous sodium sulfate, filtered, and the solvent was distilled off under reduced pressure, and the obtained crude product was purified by column chromatography (petroleum ether: ethyl acetate=3:1) to obtain 2-bromomethyl-4-fluoro-benzonitrile (86% yield). The 2-bromomethyl-4-fluorobenzonitrile (1.0 mmol) and p-toluidine (1.2 mmol) was dissolved in 50 mL of tetrahydrofuran, stirred and heated to 60° C. under reflux, and was added 0.2 g sodium ethoxide (3.0 mmol) portionwise, and refluxed further 8 hours. After the reaction was confirmed complete by TLC monitoring, the reaction was cooled to room temperature, concentrated, and added 20 mL ethyl acetate, washed with water and saturated sodium chloride solution (20 mL×3) successively to clarification, dried over anhydrous sodium sulfate, filtered, and evaporated under reduced pressure to remove the solvent. The resulting crude product was purified by column chromatography (petroleum ether: ethyl acetate=10:1) to give the intermediate compound (1.1) 2-(p-methylphenylamino) methyl-4-fluoro-benzonitrile (95% yield), mass spectrum (ESI$^+$): m/z=241.4 (M+H)$^+$.

The Following Compounds were Obtained by the Methods Similar to that in Example 1:
(1.2) 2-(p-methoxyphenylamino)methyl-4-fluorobenzonitrile mass spectrum (ESI$^+$): m/z=257.1 (M+H)$^+$
(1.3) 2-(phenylamino)methyl-4-fluoro-benzonitrile mass spectrum (ESI$^+$): m/z=227.6 (M+H)$^+$
(1.4) 2-(p-chlorophenylamino)methyl-4-fluoro-benzonitrile mass spectrum (ESI$^+$): m/z=261.1 (M+H)$^+$
(1.5) 2-(p-bromophenylamino)methyl-4-fluoro-benzonitrile mass spectrum (ESI$^+$): m/z=306.2 (M+H)$^+$
(1.6) 2-(p-tert-butylphenylamino)methyl-4-fluoro-benzonitrile mass spectrum (ESI$^+$): m/z=283.1 (M+H)$^+$
(1.7) 2-(p-cyclohexylphenylamino)methyl-4-fluoro-benzonitrile mass spectrum (ESI$^+$): m/z=309.5 (M+H)$^+$
(1.8) 2-(p-cyclopentylphenylamino)methyl-4-fluoro-benzonitrile mass spectrum (ESI$^+$): m/z=295.4 (M+H)$^+$
(1.9) 2-(3'-methylphenylamino)methyl-4-fluoro-benzonitrile mass spectrum (ESI$^+$): m/z=241.6 (M+H)$^+$
(1.10) 2-(p-ethylphenylamino)methyl-4-fluoro-benzonitrile mass spectrum (ESI$^+$): m/z=255.8 (M+H)$^+$
(1.11) 2-(3',5'-dimethoxyphenylamino)methyl-4-fluoro-benzonitrile mass spectrum (ESI$^+$): m/z=287.5 (M+H)$^+$
(1.12) 2-(p-phenoxyphenylamino)methyl-4-fluoro-benzonitrile mass spectrum (ESI$^+$): m/z=319.7 (M+H)$^+$
(1.13) 2-(p-(phenylthio)phenylamino)methyl-4-fluoro-benzonitrile mass spectrum (ESI$^+$): m/z=335.3 (M+H)$^+$
(1.14) 2-((p-methoxyphenyl)(methyl)amino)methyl-4-fluoro-benzonitrile mass spectrum (ESI$^+$): m/z=271 (M+H)$^+$
(1.15) 2-((p-methylphenyl)(methyl)amino)methyl-4-fluoro-benzonitrile mass spectrum (ESI$^+$): m/z=255 (M+H)$^+$
(1.16) 2-((p-tert-butylphenyl)(methyl)amino)methyl-4-fluoro-benzonitrile mass spectrum (ESI$^+$): m/z=297 (M+H)$^+$
(1.17) 2-((p-chlorophenyl)(propyl)amino)methyl-4-fluoro-benzonitrile mass spectrum (ESI$^+$): m/z=303 (M+H)$^+$
(1.18) 2-((p-tert-butylphenyl)(propyl)amino)methyl-4-fluoro-benzonitrile mass spectrum (ESI$^+$): m/z=325 (M+H)$^+$
(1.19) 2-((p-phenoxyphenyl)(methyl)amino)methyl-4-fluoro-benzonitrile mass spectrum (ESI$^+$): m/z=333 (M+H)$^+$
(1.20) 2-((p-cyclopentylphenyl)(propyl)amino)methyl-4-fluoro-benzonitrile mass spectrum (ESI$^+$): m/z=337 (M+H)$^+$
(1.21) 2-((p-methoxyphenyl)(propyl)amino)methyl-4-fluoro-benzonitrile mass spectrum (ESI$^+$): m/z=299 (M+H)$^+$
(1.22) 2-((p-(phenylthio)phenyl)(methyl)amino)methyl-4-fluoro-benzonitrile mass spectrum (ESI$^+$): m/z=349 (M+H)$^+$ Example 2

Synthesis of Intermediate Compound 2-(p-methylphenylamino) methyl-6-fluoro-3-cyanopyridine (2.1)

2-methyl-6-fluoro-3-cyanopyridine (10 mmol) was dissolved in 20 mL of carbon tetrachloride, and was added 0.25 g of p-toluene sulfonic acid (0.015 mmol) and 12 mmol NBS. The reaction was heated until the disappearance of starting material, then cooled to room temperature, filtered and added 20 mL of saturated aqueous ammonium chloride solution to clarification. Layers were obtained. The organic layers were washed with water and saturated sodium chloride aqueous solution (20 mL×3) successively to clarification, dried over anhydrous sodium sulfate, filtered, and evaporated under reduced pressure to remove the solvent. The obtained crude product was separated by column chromatography (petroleum ether: ethyl acetate=3:1) to obtain 2-bromomethyl-3-cyano-6-fluoropyridine (42% yield). The 2-bromomethyl-3-cyano-6-fluoropyridine (1.0 mmol) and p-toluidine (1.2 mmol) was dissolved in 5 mL of DMF, was added anhydrous potassium carbonate (3.0 mmol), stirred and heated for 5 hours, then cooled to room temperature, concentrated and the residue was purified by column chromatography (petroleum ether: ethyl acetate=10:5) to obtain the intermediate compound (2.1) 2-(p-methylphenylamino) methyl-6-fluoro-3-cyanopyridine (55% yield), mass spectrum (ESI$^+$): m/z=242 (M+H)$^+$.

The Following Compounds were Obtained by the Methods Similar to that in Example 2:
(2.2) 2-(p-methoxyphenylamino)methyl-6-fluoro-3-cyanopyridine mass spectrum (ESI$^+$): m/z=258 (M+H)$^+$
(2.3) 2-(3'-methylphenylamino)methyl-6-fluoro-3-cyanopyridine mass spectrum (ESI$^+$): m/z=242 (M+H)$^+$
(2.4) 2-((p-cyclopentylphenyl)amino)methyl-6-fluoro-3-cyanopyridine mass spectrum (ESI$^+$): m/z=296 (M+H)$^+$
(2.5) 2-((p-cyclopentylphenyl)(propyl)amino)methyl-6-fluoro-3-cyanopyridine mass spectrum (ESI$^+$): m/z=338 (M+H)$^+$
(2.6) 2-((p-chlorophenyl)(propyl)amino)methyl-6-fluoro-3-cyanopyridine mass spectrum (ESI$^+$): m/z=304 (M+H)$^+$
(2.7) 2-((p-(phenylthio)phenyl)(ethyl)amino)methyl-6-fluoro-3-cyanopyridine mass spectrum (ESI$^+$): m/z=364 (M+H)$^+$ Example 3

Synthesis of Target Compounds, such as 4-(piperazin-1-yl)-2-((p-methylphenylamino)methyl)benzonitrile(1) by using Intermediate Compounds Synthesized in Example 1 or 2 as Starting Materials The 2-(p-methylphenylamino) methyl-4-fluoro-benzonitrile (1.0 mmol) was dissolved in 5 mL DMSO, added piperazine (3.0 mmol), heated to 90° C. for 5 hours. After completion of the reaction was confirmed by TLC monitoring, the reaction was cooled to room temperature, added 20 mL of water to precipitate yellow solid, and filtered by suction. The filter cake was dried. The obtained crude product was purified by column chromatography (dichloromethane: methanol=50:1) to obtain the title compound (1, 59% yield), mass spectrum (ESI$^+$): m/z=307.4 (M+H)$^+$.

The Following Compounds were Obtained by the Methods Similar to that in Example 3:
(2) 4-(piperazin-1-yl)-2-(p-methoxyphenylamino)methyl-benzonitrile mass spectrum (ESI$^+$): m/z=323.8 (M+H)$^+$
(3) 4-(4-methylpiperazin-1-yl)-2-(p-methylphenylamino)methylbenzonitrile mass spectrum (ESI$^+$): m/z=321.7 (M+H)$^+$
(4) 4-(4-methylpiperazin-1-yl)-2-(phenylamino)methylbenzonitrile mass spectrum (ESI$^+$): m/z=307.7 (M+H)$^+$
(5) 4-(3-methylpiperazin-1-yl)-2-(p-methylphenylamino)methylbenzonitrile mass spectrum (ESI$^+$): m/z=321.8 (M+H)$^+$ (6) 4-(3-aminopiperidin-1-yl)-2-(p-methylphenylamino)methylbenzonitrile mass spectrum (ESI$^+$): m/z=321.2 (M+H)$^+$
(7) 4-(piperazin-1-yl)-2-(phenylamino)methylbenzonitrile mass spectrum (ESI$^+$): m/z=293.7 (M+H)$^+$
(8) 4-(4-methylpiperazin-1-yl)-2-(p-chlorophenylamino)methylbenzonitrile mass spectrum (ESI$^+$): m/z=341.2 (M+H)$^+$
(9) 4-(piperazin-1-yl)-2-(p-chlorophenylamino)methylbenzonitrile mass spectrum (ESI$^+$): m/z=327.4 (M+H)$^+$
(10) 4-(4-methylpiperazin-1-yl)-2-(p-methoxyphenylamino)methylbenzonitrile mass spectrum (ESI$^+$): m/z=337.3 (M+H)$^+$
(11) 4-(4-methylpiperazin-1-yl)-2-(p-cyclohexylphenylamino)methylbenzonitrile mass spectrum (ESI$^+$): m/z=389.3 (M+H)$^+$
(12) 4-(4-methylpiperazin-1-yl)-2-(p-tert-butylphenylamino)methylbenzonitrile mass spectrum (ESI$^+$): m/z=363.6 (M+H)$^+$
(13) 4-(4-methylpiperazin-1-yl)-2-(p-ethylphenylamino)methylbenzonitrile mass spectrum (ESI$^+$): m/z=335.6 (M+H)$^+$
(14) 4-(4-methylpiperazin-1-yl)-2-((p-methylphenyl)(methyl)amino)methylbenzonitrile mass spectrum (ESI$^+$): m/z=335.8 (M+H)$^+$
(15) 4-(4-methylpiperazin-1-yl)-2-((p-chlorophenyl)(propyl)amino)methylbenzonitrile mass spectrum (ESI$^+$): m/z=384.3 (M+H)$^+$
(16) 4-(4-methylpiperazin-1-yl)-2-((p-methoxyphenyl)(methyl)amino)methylbenzonitrile mass spectrum (ESI$^+$): m/z=351.6 (M+H)$^+$
(17) 4-(4-methylpiperazin-1-yl)-2-((p-tert-butylphenyl)(propyl)amino)methylbenzonitrile mass spectrum (ESI$^+$): m/z=405.5 (M+H)$^+$
(18) 4-(4-propylpiperazin-1-yl)-2-(phenylamino)methylbenzonitrile mass spectrum (ESI$^+$): m/z=335.7 (M+H)$^+$
(19) 4-(4-allylpiperazin-1-yl)-2-((p-tert-butylphenyl)(methyl)amino)methylbenzonitrile mass spectrum (ESI$^+$): m/z=403.4 (M+H)$^+$
(20) 4-(4-phenylpiperazin-1-yl)-2-((p-methoxyphenyl)(methyl)amino)methylbenzonitrile mass spectrum (ESI$^+$): m/z=413.3 (M+H)$^+$
(21) 4-(4-methylpiperazin-1-yl)-2-(p-isopropylphenylamino)methylbenzonitrile mass spectrum (ESI$^+$): m/z=349.2 (M+H)$^+$
(22) 4-(4-propylpiperazin-1-yl)-2-((p-phenoxyphenyl)(methyl)amino)methylbenzonitrile mass spectrum (ESI$^+$): m/z=441.7 (M+H)$^+$
(23) 4-(4-propylpiperazin-1-yl)-2-(p-(phenylthio)phenylamino)methylbenzonitrile mass spectrum (ESI$^+$): m/z=443.8 (M+H)$^+$
(24) 4-(4-methylpiperazin-1-yl)-2-(p-cyclopentylphenylamino)methylbenzonitrile mass spectrum (ESI$^+$): m/z=375.3(M+H)$^+$
(25) 4-(3,5-dimethylpiperazin-1-yl)-2-((p-methoxyphenyl)(methyl)amino)methylbenzonitrile mass spectrum (ESI$^+$): m/z=365.6 (M+H)$^+$
(26) 4-(N,N-dimethyl-1,3-propanediamin-1-yl)-2-(p-methylphenylamino)methylbenzonitrile mass spectrum (ESI$^+$): m/z=323.5 (M+H)$^+$
(27) 4-(N,N-dimethyl-1,3-propanediamin-1-yl)-2-(phenylamino)methylbenzonitrile mass spectrum (ESI$^+$): m/z=309.4 (M+H)$^+$
(28) 4-((2-(piperidin-1-yl)ethyl)amino)-2-(p-methylphenylamino)methylbenzonitrile mass spectrum (ESI$^+$): m/z=349.3 (M+H)$^+$
(29) 4-(N,N-dimethyl-1,3-propanediamin-1-yl)-2-(p-chlorophenylamino)methylbenzonitrile mass spectrum (ESI$^+$): m/z=343.1 (M+H)$^+$
(30) 4-(N,N-dimethyl-1,3-ethylenediamin-1-yl)-2-(p-methoxyphenylamino)methylbenzonitrile mass spectrum (ESI$^+$): m/z=339.0 (M+H)$^+$
(31) 2-((4-methoxyphenyl)amino)methyl-4-(piperidin-1-ylmethyl)aminobenzonitrile mass spectrum (ESI$^+$): m/z=351.9 (M+H)$^+$
(32) 2-((4-tert-butylphenyl)amino)methyl-4(N,N-dimethylamino)methyl)aminobenzonitrile mass spectrum (ESI$^+$): m/z=337.0 (M+H)$^+$
(33) 2-((4-tert-butylphenyl)(methyl)amino)methyl-4-(((dimethylamino)methyl)(methyl)amino)benzonitrile mass spectrum (ESI$^+$): m/z=365.7 (M+H)$^+$
(34) 2-(((4-cyclopentylphenyl)propylamino)methyl)-6-(2-(piperidin-1-yl)ethyl)amino-3-cyanopyridine mass spectrum (ESI$^+$): m/z=446.2 (M+H)$^+$
(35) 6-(4-methylpiperazin-1-yl)-2-(((p-cyclopentylphenyl)amino)methyl)-3-cyanopyridine mass spectrum (ESI$^+$): m/z=376.8 (M+H)$^+$
(36) 2-((4-methoxyphenyl)amino)methyl-6-(4-methylpiperazin-1-yl)-3-cyanopyridine mass spectrum (ESI$^+$): m/z=338.9 (M+H)$^+$
(37) 2-((4-methylphenyl)amino)methyl-6-(4-methylpiperazin-1-yl)-3-cyanopyridine mass spectrum (ESI$^+$): m/z=322.4 (M+H)$^+$
(38) 6((2-(dimethylamino)ethyl)(methyl)amino)-2-((4-methoxyphenyl)amino)methyl-3-cyanopyridine mass spectrum (ESI$^+$): m/z=339.5 (M+H)$^+$
(39) 6-(((2-(dimethylamino)ethyl)(methyl)amino)-2-((3,5-dimethoxyphenyl)amino)methyl-3-cyanopyridine mass spectrum (ESI$^+$): m/z=369.7 (M+H)$^+$
(40) 6-((2-(dimethylamino)ethyl)(methyl)amino)-2-((3-methylphenyl)amino)methyl-3-cyanopyridine mass spectrum (ESI$^+$): m/z=323.8 (M+H)$^+$
(41) 2-((4-(phenylthio)phenyl)(ethyl)amino)methyl-6-(4-propylpiperazin-1-yl)-3-cyanopyridine mass spectrum (ESI$^+$): m/z=472.4 (M+H)$^+$
(42) 2-(((4-bromophenyl)amino)methyl)-4-(4-methylpiperazin-1-yl)benzonitrile mass spectrum (ESI$^+$): m/z=386.6 (M+H)$^+$ Example 4

The Anti-HCV Activity Assay for the Compounds of the Present Invention

100 μL Huh7.5 cells were seeded in 96-well cell culture plate to 1×10$^5$/mL density, cultured in an incubator at 37° C. under the condition of 5% CO$_2$ and saturated humidity for 6 hrs. Huh7.5 cells were then infected by viral solution containing HCV virus particles, and solutions of compound of the present invention at a concentration of 10 μmol/L liquid were added respectively, cultured for further 96 hrs, and then total RNA was extracted from the cells. Amount of HCV RNA in cells was determined by one-step quantitative RT-PCR, and compared to RNA levels of the virus control group to calculate the inhibition rate of compounds on HCV. Compound results are shown in Table 1.

Example 5

Synthesis of Intermediate Compound 4-fluoro-2-(4-(4-methoxyphenyl)piperazin-1-yl)methylbenzonitrile (5.1)

1.35 g 2-methyl-4-fluorobenzonitrile (10 mmol) was dissolved in 20 mL of carbon tetrachloride, and added 0.25 g of p-toluene sulfonic acid (0.015 mmol) and 2.15 g N-bromo succinimide (NBS) (12 mmol). The reaction was heated for 4 hours to complete the reaction. The reaction was cooled to room temperature, filtered, and added 20 mL saturated ammonium chloride solution. Layers were obtained. The organic layer was washed with water and saturated sodium chloride aqueous solution (20 mL×3) successively to clarification, dried over anhydrous sodium sulfate, filtered and evaporated under reduced pressure to remove solvents. The resulting crude product was purified by column chromatography (petroleum ether: ethyl acetate=3:1) to obtain 2-bromomethyl-4-fluorobenzonitrile (86% yield). 2-bromomethyl-4-fluorobenzonitrile (1.0 mmol) and 1-(4-methoxyphenyl)-piperazine (1.2 mmol) was dissolved in 50 mL of tetrahydrofuran, added potassium carbonate (3.0 mmol), stirred and heated at reflux. After the completion of the reaction was confirmed by TLC monitoring, the reaction was cooled to room temperature, concentrated, added 20 mL ethyl acetate, washed with water and saturated sodium chloride solution successively to clarification, dried over anhydrous sodium sulfate, filtered, and purified by column chromatography (petroleum ether: ethyl acetate=5:1) to obtain the intermediate compound (5.1) 4-fluoro-2-(4-(4-methoxyphenyl)piperazin-1-yl)methylbenzonitrile(73% yield), mass spectrum (ESI$^+$): m/z=326.5 (M+H)$^+$.

The Following Compounds were Obtained by the Methods Similar to that in Example 5:

(5.2) 4-fluoro-2-(4-(4-methylphenyl)piperazin-1-yl)methylbenzonitrile mass spectrum (ESI$_+$): m/z=310.6 (M+H)$^+$
(5.3) 2-(4-phenylpiperazin-1-yl)methyl-4-fluoro-benzonitrile mass spectrum (ESI$^+$): m/z=296.3 (M+H)$^+$
(5.4) 4-fluoro-2-(4-(4-chlorophenyl)piperazin-1-yl)methylbenzonitrile mass spectrum (ESI$^+$): m/z=330.5 (M+H)$^+$
(5.5) 4-fluoro-2-(4-(4-bromophenyl)piperazin-1-yl)methylbenzonitrile mass spectrum (ESI$^+$): m/z=374.8 (M+H)$^+$
(5.6) 4-fluoro-2-(4-(4-tert-butylphenyl)piperazin-1-yl)methylbenzonitrile mass spectrum (ESI$^+$): m/z=352.5 (M+H)$^+$
(5.7) 4-fluoro-2-(4-(4-cyclohexylphenyl)piperazin-1-yl)methylbenzonitrile mass spectrum (ESI$^+$): m/z=378.3 (M+H)$^+$
(5.8) 4-fluoro-2-(4-(4-cyclopentylphenyl)piperazin-1-yl)methylbenzonitrile mass spectrum (ESI$^+$): m/z=364.4 (M+H)$^+$
(5.9) 4-fluoro-2-(4-(3-methylphenyl)piperazin-1-yl)methylbenzonitrile mass spectrum (ESI$^+$): m/z=310.5 (M+H)$^+$
(5.10) 4-fluoro-2-(4-(4-ethylphenyl)piperazin-1-yl)methylbenzonitrile mass spectrum (ESI$^+$): m/z=324.7 (M+H)$^+$
(5.11) 4-fluoro-2-(4-(3,5-dimethoxyphenyl)piperazin-1-yl)methylbenzonitrile mass spectrum (ESI$^+$): m/z=356.4 (M+H)$^+$
(5.12) 4-fluoro-2-(4-(4-isopropylphenyl)piperazin-1-yl)methylbenzonitrile mass spectrum (ESI$^+$): m/z=338.6 (M+H)$^+$
(5.13) 4-fluoro-2-(4-(3,4-dimethylphenyl)piperazin-1-yl)methylbenzonitrile mass spectrum (ESI$^+$): m/z=324.5 (M+H)$^+$
(5.14) 4-fluoro-2-(4-(3-methyl-4-chlorophenyl)piperazin-1-yl)methylbenzonitrile mass spectrum (ESI$^+$): m/z=344.8 (M+H)$^+$
(5.15) 4-fluoro-2-(4-(4-hydroxylphenyl)piperazin-1-yl)methylbenzonitrile mass spectrum (ESI$^+$): m/z=312.7 (M+H)$^+$
(5.16) 4-fluoro-2-(4-(4-methylaminophenyl)piperazin-1-yl)methylbenzonitrile mass spectrum (ESI$^+$): m/z=325.2 (M+H)$^+$
(5.17) 4-fluoro-2-(4-(4-dimethylaminophenyl)piperazin-1-yl)methylbenzonitrile mass spectrum (ESI$^+$): m/z=339.6 (M+H)$^+$
(5.18) 4-fluoro-2-(4-(3-methyl-4-cyanophenyl)piperazin-1-yl)methylbenzonitrile mass spectrum (ESI$^+$): m/z=335.2 (M+H)$^+$
(5.19) 4-fluoro-2-(4-(4-tert-butylphenyl)piperidin-1-yl)methylbenzonitrile mass spectrum (ESI$^+$): m/z=351.5 (M+H)$^+$
(5.20) 4-fluoro-2-(4-(4-methoxyphenyl)piperidin-1-yl)methylbenzonitrile mass spectrum (ESI$^+$): m/z=325.1 (M+H)$^+$
(5.21) 4-fluoro-2-(4-(4-methylphenyl)piperidin-1-yl)methylbenzonitrile mass spectrum (ESI$^+$): m/z=309.3 (M+H)$^+$
(5.22) 4-fluoro-2-(4-(4-chlorophenyl)piperidin-1-yl)methylbenzonitrile mass spectrum (ESI$^+$): m/z=329.2 (M+H)$^+$
(5.23) 4-fluoro-2-(4-phenylpiperidin-1-yl)methylbenzonitrile mass spectrum (ESI$^+$): m/z=295.2 (M+H)$^+$
(5.24) 4-fluoro-2-(4-(4-trifluoromethylphenyl)-piperazin-1-yl)methylbenzonitrile mass spectrum (ESI$^+$): m/z=364.1 (M+H)$^+$ Example 6

Synthesis of target compound for example, 4-((N',N'-dimethyl-1,2-ethylenediamin-1-yl)-2-(4-(4-methoxyphenyl)piperazin-1-yl)methylbenzonitrile(VI-1) by reacting intermediate compound synthesized in Example 5 as starting materials with the corresponding amine, 4-fluoro-2-(4-(4-methoxyphenyl)piperazin-1-yl)methylbenzonitrile (1.0 mmol) was dissolved in 5 mL DMSO, added N,N-dimethylethylenediamine (3.0 mmol). The reaction was heated to 90° C. for 5 hours. After the completion of the reaction was confirmed by TLC monitoring, the reaction was cooled to room temperature, added 20 mL of water to precipitate yellow solid, filtered by suction. The filter cake was dried. The obtained crude product was purified by column chromatography (dichloromethane: methanol=10:1) to obtain the title compound (43, 59% yield), mass spectrum (ESI$^+$): m/z=394.3 (M+H)$^+$.

The Following Compounds were Obtained by the Methods Similar to that in Example 6:
(VI-2) 4-(((piperidin-1-yl)methyl)amino)-2-(4-(4-methoxyphenyl)piperazin-1-yl)methylbenzonitrile mass spectrum (ESI$^+$): m/z=420.3 (M+H)$^+$
(VI-3) 4-((4-methyl)piperazin-1-yl)-2-(4-(4-methoxyphenyl)piperazin-1-yl)methylbenzonitrile mass spectrum (ESI$^+$): m/z=406.4 (M+H)$^+$
(VI-4) 4-((4-methyl)piperazin-1-yl)-2-(4-(4-methylphenyl)piperazin-1-yl)methylbenzonitrile mass spectrum (ESI$^+$): m/z=390.5 (M+H)$^+$
(VI-5) 4-(piperazin-1-yl)-2-(4-(4-methoxyphenyl)piperazin-1-yl)methylbenzonitrile mass spectrum (ESI$^+$): m/z=392.1 (M+H)$^+$
(VI-6) 4-(piperazin-1-yl)-2-(4-(4-methylphenyl)piperazin-1-yl)methylbenzonitrile mass spectrum (ESI$^+$): m/z=376.4 (M+H)$^+$
(VI-7) 4-(3-aminopiperidin-1-yl)-2-((4-(4-methylphenyl)piperazin-1-yl)methyl)benzonitrile mass spectrum (ESI$^+$): m/z=390.6 (M+H)$^+$
(VI-8) 4-(piperazin-1-yl)-2-(4-(4-phenyl)piperazin-1-yl)methylbenzonitrile mass spectrum (ESI$^+$): m/z=362.3 (M+H)$^+$
(VI-9) 4-(4-methylpiperazin-1-yl)-2-(4-(4-chlorophenyl)piperazin-1-yl)methylbenzonitrile mass spectrum (ESI$^+$): m/z=410.5 (M+H)$^+$ (VI-10) 4-(piperazin-1-yl)-2-(4-(4-chlorophenyl)piperazin-1-yl)methylbenzonitrile mass spectrum (ESI$^+$): m/z=396.8 (M+H)$^+$ (VI-11) 4-(4-methylpiperazin-1-yl)-2-(4-(3,4-dimethylphenyl)piperazin-1-yl)methylbenzonitrile mass spectrum (ESI$^+$): m/z=404.7 (M+H)$^+$ (VI-12) 4-(4-methylpiperazin-1-yl)-2-(4-(4-cyclohexylphenyl)piperazin-1-yl)methylbenzonitrile mass spectrum (ESI$^+$): m/z=458.4 (M+H)$^+$ (VI-13) 4-(4-methylpiperazin-1-yl)-2-(4-(4-tert-butylphenyl)piperazin-1-yl)methylbenzonitrile mass spectrum (ESI$^+$): m/z=432.3 (M+H)$^+$ (VI-14) 4-(4-methylpiperazin-1-yl)-2-(4-(4-ethylphenyl)piperazin-1-yl)methylbenzonitrile mass spectrum (ESI$^+$): m/z=404.5 (M+H)$^+$ (VI-15) 4-(piperazin-1-yl)-2-(4-(3 -methyl4-chlorophenyl)piperazin-1-yl)methylbenzonitrile mass spectrum (ESI$^+$): m/z=410.9 (M+H)$^+$ (VI-16) 4-(4-methylpiperazin-1-yl)-2-(4-(4-isopropylphenyl)piperazin-1-yl)methylbenzonitrile mass spectrum (ESI$^+$): m/z=418.6 (M+H)$^+$ (VI-17) 4-(4-methylpiperazin-1-yl)-2-(4-(4-(methylthio)phenyl)piperazin-1-yl)methylbenzonitrile mass spectrum (ESI$^+$): m/z=422.3 (M+H)$^+$ (VI-18) 4-(4-methylpiperazin-1-yl)-2-(4-(4-bromophenyl)piperazin-1-yl)methylbenzonitrile mass spectrum (ESI$^+$): m/z=454.4 (M+H)$^+$ (VI-19) 4-(4-methylpiperazin-1-yl)-2-(4-(4-hydroxylphenyl)piperazin-1-yl)methylbenzonitrile mass spectrum (ESI$^+$): m/z=392.3 (M+H)$^+$ (VI-20) 4-(4-methylpiperazin-1-yl)-2-(4-(4-methylaminophenyl)piperazin-1-yl)methylbenzonitrile mass spectrum (ESI$^+$): m/z=405.5 (M+H)$^+$ (VI-21) 4-(4-methylpiperazin-1-yl)-2-(4-(4-dimethylaminophenyl)piperazin-1-yl)methylbenzonitrile mass spectrum (ESI$^+$): m/z=419.7 (M+H)$^+$ (VI-22) 4((2-(dimethylamino)ethyl)(methyl)amino)-2-(4-(4-(pyrrolidin-1-yl)phenyl)piperazin-1-yl)methylbenzonitrile mass spectrum (ESI$^+$): m/z=447.5 (M+H)$^+$ (VI-23) 4-(4-methylpiperazin-1-yl)-2-(4-(3-methyl-4-cyanophenyl)piperidin-1-yl)methylbenzonitrile mass spectrum (ESI$^+$): m/z=414.8 (M+H)$^+$ (VI-24) 4-(4-methylpiperazin-1-yl)-2-(4-(4-cyclopentylphenyl)piperazin-1-yl)methylbenzonitrile mass spectrum (ESI$^+$): m/z=444.4(M+1)$^+$ (VI-25) 4-(2,6-dimethylpiperazin-1-yl)-2-(4-p-methoxyphenyl)piperazin-1-yl)methylbenzonitrile mass spectrum (ESI$^+$): m/z=420.2 (M+H)$^+$ (VI-26) 4-(N',N'-dimethyl-1,3-propanediamin-1-yl)-2-(4-p-methylphenylpiperazin-1-yl)methylbenzonitrile mass spectrum (ESI$^+$): m/z=392.3 (M+H)$^+$ (VI-27) 4-(N',N'-dimethyl-1,3-propanediamin-1-yl)-2-(4-phenylpiperazin-1-yl)methylbenzonitrile mass spectrum (ESI$^+$): m/z=378.4 (M+H)$^+$ (VI-28) 4-(N',N'-dimethyl-1,2-ethylenediamin-1-yl)-2-(4-p-trifluoromethylphenyl-piperazin-1-yl)methylbenzonitrile mass spectrum (ESI$^+$): m/z=432.5 (M+H)$^+$ (VI-29) 4-(N',N'-dimethyl-1,3-propanediamin-1-yl)-2-(4-p-chlorophenylpiperazin-1-yl)methylbenzonitrile mass spectrum (ESI$^+$): m/z=412.9 (M+H)$^+$ (VI-30) 4-(N',N'-dimethyl-1,2-ethylenediamin-1-yl)-2-(4-p-methoxyphenylpiperazin-1-yl)methylbenzonitrile mass spectrum (ESI$^+$): m/z=394.6 (M+H)$^+$ (VI-31) 4-(N,N',N'-trimethyl-1,2-ethylenediamin-1-yl)-2-(4-p-methoxyphenylpiperazin-1-yl)methylbenzonitrile mass spectrum (ESI$^+$): m/z=408.5 (M+H)$^+$ (VI-32) 4-(N,N',N'-trimethyl1,3-propanediamin-1-yl)-2-(4-p-cyclohexylphenylpiperazin-1-yl)methylbenzonitrile mass spectrum (ESI$^+$): m/z=474.9 (M+H)$^+$ (VI-33) 2-(4-(4-tert-butylphenyl)piperazin-1-yl)methyl-4-((N,N-dimethylamino)methyl)amino-benzonitrile mass spectrum (ESI$^+$): m/z=406.6 (M+H)$^+$ (VI-34) 2-(4-(4-bromophenyl)piperazin-1-yl)methyl-4-(4-methylpiperazin-1-yl)benzonitrile mass spectrum (ESI$^+$): m/z=454.2 (M+H)$^+$ (VI-35) 4-(N,N',N'-trimethyl-1,2-ethylenediamin-1-yl)-2-(4-p-chlorophenylpiperazin-1-yl)methylbenzonitrile mass spectrum (ESI$^+$): m/z=412.8 (M+H)$^+$ (VI-36) 4-((methyl)((piperidin-1-yl)-methyl)amino)-2-(4-p-methylphenylpiperazin-1-yl)methylbenzonitrile mass spectrum (ESI$^+$): m/z=418.8 (M+H)$^+$ (VI-37) 4-((methyl)((pyrrolidin-1-yl)-methyl)amino)-2-(4-p-methylphenylpiperazin-1-yl)methylbenzonitrile mass spectrum (ESI$^+$): m/z=404.6 (M+H)$^+$ (VI-38) 4-(4-methylpiperazin-1-yl)-2-(4-(4-tert-butylphenyl)piperidin-1-yl)methylbenzonitrile mass spectrum (ESI$^+$): m/z=431.2 (M+H)$^+$ (VI-39) 4-(N,N',N'-trimethyl-1,2-ethylenediamin-1-yl)-2-(4-p-chlorophenylpiperidin-1-yl)methylbenzonitrile mass spectrum (ESI$^+$): m/z=411.0 (M+H)$^+$ (VI-40) 4-((methyl)((morpholine-4-yl)ethyl))amino-2-(4-p-methylphenylpiperidin-1-yl)methylbenzonitrile mass spectrum (ESI$^+$): m/z=433.3 (M+H)$^+$ (VI-41) 4-((methyl)((pyrrolidin-1-yl)ethyl))amino-2-(4-p-methoxyphenylpiperidin-1-yl)methylbenzonitrile mass spectrum (ESI$^+$): m/z=433.5 (M+H)$^+$ (VI-42) 4-((methyl)((1-ethylpyrrolidin-2-yl)methyl))amino-2-(4-phenylpiperidin-1-yl)methylbenzonitrile mass spectrum (ESI$^+$): m/z=417.5 (M+H)$^+$ (VI-43) 4-((ethyl)((pyrrolidin-1-yl)ethyl))amino-2-(4-p-methylphenylpiperazin-1-yl)methylbenzonitrile mass spectrum (ESI$^+$): m/z=432.6 (M+H)$^+$ (VI-44) 4-((3-dimethylamino)pyrrolidin-1-yl)-2-(4-p-chlorophenylpiperazin-1-yl)methylbenzonitrile mass spectrum (ESI$^+$): m/z=424.1 (M+H)$^+$ (VI-45) 4-(N,N',N'-trimethyl-1,2-ethylenediamin-1-yl)-2-(3,4-dimethoxyphenylpiperazin-1-yl)methylbenzonitrile mass spectrum (ESI$^+$): m/z=438.7 (M+H)$^+$ (VI-46) 4-(1-(pyrrolidin-1-yl)propyl-2-yl)amino-2-(4-p-methoxyphenylpiperazin-1-yl)methylbenzonitrile mass spectrum (ESI$^+$): m/z=434.3 (M+H)$^+$ (VI-47) 4-(N,N',N'-trimethyl-1,2-ethylenediamin-1-yl)-2-(4-trifluoromethoxyphenylpiperazin-1-yl)methylbenzonitrile mass spectrum (ESI$^+$): m/z=462.5 (M+H)$^+$

The invention claimed is:

1. A compound having the structure shown in the following formula (I)-, formula VI or a pharmaceutically acceptable salt thereof:

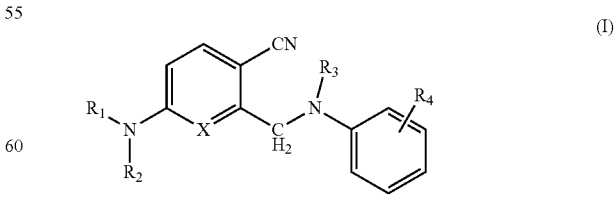

(I)

wherein $R_1$ is amino C1-C4 alkyl wherein the amino is substituted by $R_8$ and/or $R_9$, $R_8$ and $R_9$ are H or C1-C4 alkyl, or, form a six-membered ring together with the nitrogen atom to which they are bonded, the said six-membered ring is selected from piperazine or piperidine, $R_2$ is H or C1-C4 alkyl;

or $R_1$ and $R_2$ form a six-membered ring together with the nitrogen atom to which they are bonded, the said six-membered ring is selected from substituted or unsubstituted piperazine or piperidine, wherein the piperazine or piperidine is substituted by C1-C4 alkyl, C1-C4 alkoxy, C2-C4 alkenyl, phenyl, amino or halogen;

$R_3$ is H or C1-C4 alkyl;

$R_4$ is H or one or more substituents selected from a group consisting of C1-C4 alkyl, C5-C6 cycloalkyl, C1-C4 alkoxy, phenoxy, phenylthio and halogen at any available position(s) on the phenyl ring;

X is N or C;

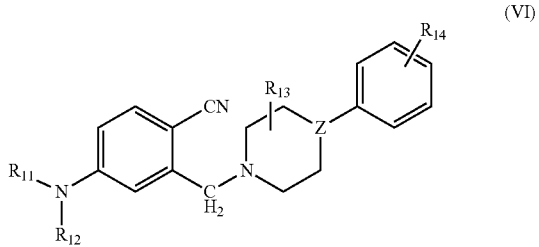

wherein $R_{11}$ is amino C1-C4 alkyl wherein the amino is substituted by $R_{18}$ and/or $R_{19}$, $R_{18}$ and $R_{19}$ are H or C1-C4 alkyl, or, form a saturated five- or six-membered ring together with the nitrogen atom to which they are bonded, the said saturated five- or six-membered ring is selected from a group consisting of pyrrolidine, morpholine, piperazine and piperidine, $R_{12}$ is H or C1-C4 alkyl;

or $R_{11}$ is

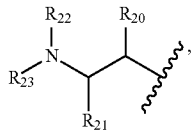

$R_{23}$ is H or C1-C4 alkyl, $R_{22}$ and $R_{21}$ are H or C1-C4 alkyl, or $R_{22}$ and $R_{21}$ form a saturated five- or six-membered ring together with the nitrogen atom to which they are bonded, the said saturated five- or six-membered ring is selected from a group consisting of pyrrolidine, morpholine, piperazine and piperidine, $R_{20}$ is H or C1-C4 alkyl, $R_{12}$ is H or C1-C4 alkyl;

or $R_{11}$ and $R_{12}$ form a saturated five- or six-membered ring together with the nitrogen atom to which they are bonded, the said saturated five- or six-membered ring selected from a group consisting of pyrrolidine, morpholine, piperazine and piperidine, wherein the saturated five- or six-membered ring is substituted by C1-C4 alkyl, C1-C4 alkoxy, C2-C4 alkenyl, phenyl, amino, methylamino, dimethylamino or halogen;

$R_{13}$ is H or C1-C4 alkyl;

$R_{14}$ is H or one or more substituents selected from a group consisting of C1-C4 alkyl, C5-C6 cycloalkyl, C1-C4 alkoxy, phenoxy, methylthio, phenylthio, amino, methylamino, dimethylamino, hydroxy, trifluoromethyl, trifluoromethoxy, cyano or halogen at any available position(s) of the phenyl ring;

Z is N or C.

2. The compound as claimed in claim 1, being a compound having the structure as shown in the following formula II or a pharmaceutically acceptable salt thereof:

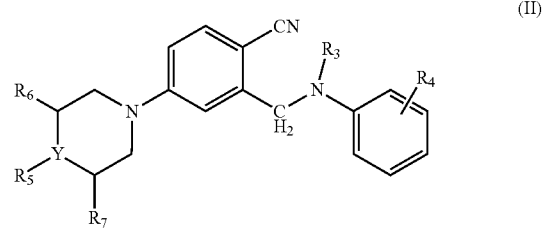

wherein $R_3$ is H or C1-C4 alkyl, $R_4$ is H or one or more substituents selected from a group consisting of straight-chain or branched-chain C1-C4 alkyl, C5-C6 cycloalkyl, $C_1$-C4 alkoxy, phenoxy, phenylthio and halogen at any available position(s) on the phenyl ring, $R_5$ is H, C1-C4 alkyl, C2-C4 alkenyl, or phenyl, $R_6$ and $R_7$ are H, C1-C4 alkyl or amino respectively or simultaneously, Y is N or C.

3. The compound as claimed in claim 1, being a compound having the structure as shown in the general formula III or a pharmaceutically acceptable salt thereof:

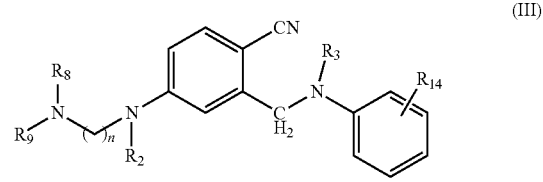

wherein, $R_2$ is H or C1-C4 alkyl, $R_8$ and $R_9$ are H or C1-C4 alkyl, or, form a six-membered ring together with the nitrogen atom to which they are bonded, said six-membered ring is selected from piperazine or piperidine, $R_3$ is H or C1-C4 alkyl, $R_4$ is H or one or more substituents selected from a group consisting of straight-chain or branched-chain C1-C4 alkyl, C5-C6 cycloalkyl, C1-C4 alkoxy, phenoxy, phenylthio and halogen at any available position(s) on the phenyl ring, n is an integer of 1-4.

4. The compound as claimed in claim 1, being a compound having the structure as shown in the general formula IV or a pharmaceutically acceptable salt thereof:

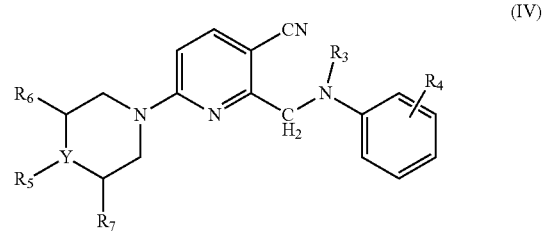

wherein $R_3$ is H or C1-C4 alkyl, $R_4$ is H or one or more substituents selected from a group consisting of straight-chain or branched-chain C1-C4 alkyl, C5-C6 cycloalkyl, C1-C4 alkoxy, phenoxy, phenylthio or halogen at any available position(s) on the phenyl ring, $R_5$ is H, C1-C4 alkyl, C2-C4 alkenyl, or phenyl, $R_6$ and $R_7$ are H, C1-C4 alkyl or amino respectively or simultaneously, Y is N or C.

5. The compound as claimed in claim 1, being a compound having the structure as shown in the general formula V or a pharmaceutically acceptable salt thereof:

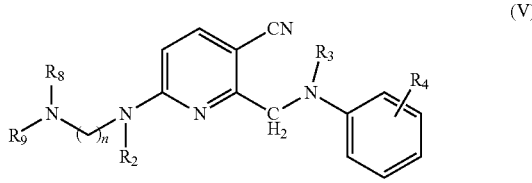

(V)

wherein, $R_2$ is H or C1-C4 alkyl, $R_8$ and $R_9$ are H or C1-C4 alkyl, or, form a six-membered ring together with the nitrogen atom to which they are bonded, the said six-membered ring is selected from piperazine or piperidine, $R_3$ is H or C1-C4 alkyl, $R_4$ is H or one or more substituents selected from a group consisting of straight-chain or branched-chain C1-C4 alkyl, C5-C6 cycloalkyl, C1-C4 alkoxy, phenoxy, phenylthio and halogen at any available position(s) on the phenyl ring, n is an integer of 1-4.

6. The compound as claimed in claim 1 is:
4-(piperazin-1-yl)-2-((p-methylphenylamino)methyl) benzonitrile;
4-(piperazin-1-yl)-2-(p-methoxyphenylamino)methylbenzonitrile;
4-(4-methylpiperazin-1-yl)-2-(p-methylphenylamino) methylbenzonitrile;
4-(4-methylpiperazin-1-yl)-2-(phenylamino)methylbenzonitrile;
4-(3-methylpiperazin-1-yl)-2-(p-methylphenylamino) methylbenzonitrile;
4-(3-aminopiperidin-1-yl)-2-(p-methylphenylamino) methylbenzonitrile;
4-(piperazin-1-yl)-2-(phenylamino)methylbenzonitrile;
4-(4-methylpiperazin-1-yl)-2-(p-chlorophenylamino) methylbenzonitrile;
4-(piperazin-1-yl)-2-(p-chlorophenylamino)methylbenzonitrile;
4-(4-methylpiperazin-1-yl)-2-(p-methoxyphenylamino) methylbenzonitrile;
4-(4-methylpiperazin-1-yl)-2-(p-cyclohexylphenylamino)methylbenzonitrile;
4-(4-methylpiperazin-1-yl)-2-(p-tert-butylphenylamino) methylbenzonitrile;
4-(4-methylpiperazin-1-yl)-2-(p-ethylphenylamino)methylbenzonitrile;
4-(4-methylpiperazin-1-yl)-2-((p-methylphenyl)(methyl) amino)methylbenzonitrile;
4-(4-methylpiperazin-1-yl)-2-((p-chlorophenyl)(propyl) amino)methylbenzonitrile;
4-(4-methylpiperazin-1-yl)-2-((p-methoxyphenyl) (methyl)amino)methylbenzonitrile;
4-(4-methylpiperazin-1-yl)-2-((p-tert-butylphenyl)(propyl)amino)methylbenzonitrile;
4-(4-propylpiperazin-1-yl)-2-(phenylamino)methylbenzonitrile;
4-(4-allylpiperazin-1-yl)-2-((p-tert-butylphenyl)(methyl) amino)methylbenzonitrile;
4-(4-phenylpiperazin-1-yl)-2-((p-methoxyphenyl) (methyl)amino)methylbenzonitrile;
4-(4-methylpiperazin-1-yl)-2-(p-isopropylphenylamino) methylbenzonitrile;
4-(4-propylpiperazin-1-yl)-2-((p-phenoxyphenyl) (methyl)amino)methylbenzonitrile;
4-(4-propylpiperazin-1-yl)-2-(p-(phenylthio)phenylamino)methylbenzonitrile;
4-(4-methylpiperazin-1-yl)-2-(p-cyclopentylphenylamino)methylbenzonitrile;
4-(3,5-dimethylpiperazin-1-yl)-2-((p-methoxyphenyl) (methyl)amino)methylbenzonitrile;
4-(N,N-dimethyl-1,3-propanediamin-1-yl)-2-(p-methylphenylamino)methylbenzonitrile;
4-(N,N-dimethyl-1,3-propanediamin-1-yl)-2-(phenylamino)methylbenzonitrile;
4-((2-(piperidin-1-yl)ethyl)amino)-2-(p-methylphenylamino)methylbenzonitrile;
4-(N,N-dimethyl-1,3-propanediamin-1-yl)-2-(p-chlorophenylamino)methylbenzonitrile;
4-(N,N-dimethyl-1,3-ethylenediamin-1-yl)-2-(p-methoxyphenylamino)methylbenzonitrile;
2-((4-methoxyphenyl)amino)methyl-4-(piperidin-1-ylmethyl)aminobenzonitrile;
2-((4-tert-butylphenyl)amino)methyl-4-((N,N-dimethylamino)methyl)aminobenzonitrile;
2-((4-tert-butylphenyl)(methyl)amino)methyl-4-(((dimethylamino)methyl)(methyl)amino)benzonitrile;
2-(((4-cyclopentylphenyl)propylamino)methyl)-6-(2-(piperidin-1-yl)ethyl)amino-3-cyanopyridine;
6-(4-methylpiperazin-1-yl)-2-((4-cyclopentylphenylamino)methyl)-3-cyanopyridine;
2-((4-methoxyphenyl)amino)methyl-6-(4-methylpiperazin-1-yl)-3-cyanopyridine;
2-((4-methylphenyl)amino)methyl-6-(4-methylpiperazin-1-yl)-3-cyanopyridine;
6-((2-(dimethylamino)ethyl)(methyl)amino)-2-((4-methoxyphenyl)amino)methyl-3-cyanopyridine;
6-(((2-(dimethylamino)ethyl)(methyl)amino)-2-((3,5-dimethoxyphenyl)amino)methyl-3-cyanopyridine;
6-((2-(dimethylamino)ethyl)(methyl)amino)-24(3-methylphenyl)amino)methyl-3-cyanopyridine;
2((4-(phenylthio)phenyl)(ethyl)amino)methyl-6-(4-propylpiperazin-1-yl)-3-cyanopyridine;
2-(((4-bromophenyl)amino)methyl)-4-(4-methylpiperazin-1-yl)benzonitrile;
4-((N',N'-dimethyl-1,2-ethylenediamin-1-yl)-2-(4-(4-methoxyphenyl)piperazin-1-yl)methylbenzonitrile;
4-(((piperidin-1-yl)methy)amino)-2-(4-(4-methoxyphenyl)piperazin-1-yl)methylbenzonitrile;
4-((4-methyl)piperazin-1-yl)-2-(4-(4-methoxyphenyl) piperazin-1-yl)methylbenzonitrile;
4-((4-methyl)piperazin-1-yl)-2-(4-(4-methylphenyl)piperazin-1-yl)methylbenzonitrile;
4-(piperazin-1-yl)-2-(4-(4-methoxyphenyl)piperazin-1-yl)methylbenzonitrile;
4-(piperazin-1-yl)-2-(4-(4-methylphenyl)piperazin-1-yl) methylbenzonitrile;
4-(3-aminopiperidin-1-yl)-2-((4-(4-methylphenyl)piperazin-1-yl)methyl)benzonitrile;
4-(piperazin-1-yl)-2-(4-(4-phenyl)piperazin-1-yl)methylbenzonitrile;
4-(4-methylpiperazin-1-yl)-2-(4-(4-chlorophenyl)piperazin-1-yl)methylbenzonitrile;
4-(piperazin-1-yl)-2-(4-(4-chlorophenyl)piperazin-1-yl) methylbenzonitrile;

4-(4-methylpiperazin-1-yl)-2-(4-(3,4-dimethylphenyl)piperazin-1-yl)methylbenzonitrile;
4-(4-methylpiperazin-1-yl)-2-(4-(4-cyclohexylphenyl)piperazin-1-yl)methylbenzonitrile;
4-(4-methylpiperazin-1-yl)-2-(4-(4-tert-butylphenyl)piperazin-1-yl)methylbenzonitrile;
4-(4-methylpiperazin-1-yl)-2-(4-(4-ethylphenyl)piperazin-1-yl)methylbenzonitrile;
4-(piperazin-1-yl)-2-(4-(3-methyl4-chlorophenyl)piperazin-1-yl)methylbenzonitrile;
4-(4-methylpiperazin-1-yl)-2-(4-(4-isopropylphenyl)piperazin-1-yl)methylbenzonitrile;
4-(4-methylpiperazin-1-yl)-2-(4-(4-(methylthio)phenyl)piperazin-1-yl)methylbenzonitrile;
4-(4-methylpiperazin-1-yl)-2-(4-(4-bromophenyl)piperazin-1-yl)methylbenzonitrile;
4-(4-methylpiperazin-1-yl)-2-(4-(4-hydroxylphenyl)piperazin-1-yl)methylbenzonitrile;
4-(4-methylpiperazin-1-yl)-2-(4-(4-methylaminophenyl)piperazin-1-yl)methylbenzonitrile;
4-(4-methylpiperazin-1-yl)-2-(4-(4-dimethylaminophenyl)piperazin-1-yl)methylbenzonitrile;
4-((2-(dimethylamnino)ethyl)(methy)amnino)-2-(4-(4-(pyrrolidin-1-yl)phenyl)piperazin-1-yl)methylbenzonitrile;
4-(4-methylpiperazin-1-yl)-2-(4-(3-methyl-4-cyanophenyl)piperidin-1-yl)methylbenzonitrile;
4-(4-methylpiperazin-1-yl)-2-(4-(4-cyclopentylphenyl)piperazin-1-yl)methylbenzonitrile;
4-(2,6-dimethylpiperazin-1-yl)-2-(4-p-methoxyphenyl)piperazin-1-yl)methylbenzonitrile;
4-(N',N'-dimethyl-1,3-propanediamin-1 -yl))-2-(4-p-methylphenylpiperazin-1-yl)methylbenzonitrile;
4-(N',N'-dimethyl-1,3-propanediamin-1 -yl))-2-(4-phenylpiperazin-1-yl)methylbenzonitrile;
4-(N',N'-dimethyl-1,2-ethylenediamin-1-yl)-2-(4-p-trifluoromethylphenyl-piperazin-1-yl)methylbenzonitrile;
4-(N',N'-dimethyl-1,3-propanediamin-1-yl))-2-(4-p-chlorophenylpiperazin-1-yl)methylbenzonitrile;
4-(N',N'-dimethyl-1,2-ethylenediamin-1-yl)-2-(4-p-methoxyphenylpiperazin-1-yl)methylbenzonitrile;
4-(N,N',N'-trimethyl-1,2-ethylenediamin-1-yl)-2-(4-p-methoxyphenylpiperazin-1-yl)methylbenzonitrile;
4-(N,N',N'-trimethyl-1,3-propanediamin-1-yl)-2-(4-p-cyclohexylphenylpiperazin-1-yl)methylbenzonitrile;
2-(4-(4-tert-butylphenyl)piperazin-1-yl)methyl-4-((N,N-dimethylamino)methyl)amino-benzonitrile;
2-(4-(4-bromophenyl)piperazin-1-yl)methyl-4-(4-methylpiperazin-1-yl)benzonitrile;
4-(N,N',N'-trimethyl-1,2-ethylenediamin-1-yl))-2-(4-p-chlorophenylpiperazin-1-yl)methylbenzonitrile;
4-((methyl)((piperidin-1-yl))-methyl)amino)-2-(4-p-methylphenylpiperazin-1-yl)methylbenzonitrile;
4-((methyl)((pyrrolidin-1-yl))-methyl)amino)-2-(4-p-methylphenylpiperazin-1-yl)methylbenzonitrile;
4-(4-methylpiperazin-1-yl)-2-(4-(4-tert-butylphenyl)piperidin-1-yl)methylbenzonitrile;
4-(N,N',N'-trimethyl-1,2-ethylenediamin-1-yl))-2-(4-p-chlorophenylpiperidin-1-yl)methylbenzonitrile;
4-((methyl)((morpholine-4-yl)ethyl))amino)-2-(4-p-methylphenylpiperidin-1-yl)methylbenzonitrile;
4-((methyl)((pyrrolidin-1-yl)ethyl))amino-2-(4-p-methoxyphenylpiperidin-1-yl)methylbenzonitrile;
4-((methyl)((1-ethylpyrrolidin-2-yl)methyl))amino-2-(4-phenylpiperazin-1-yl)methylbenzonitrile;
4-((ethyl)((pyrrolidin-1-yl)ethyl))amino-2-(4-p-methylphenylpiperazin-1-yl)methylbenzonitrile;
4-((3-dimethylamino)pyrrolidin-1-yl)-2-(4-p-chlorophenylpiperazin-1-yl)methylbenzonitrile;
4-(N,N',N'-trimethyl-1,2-ethylenediamin-1-yl)-2-(3,4-dimethoxyphenylpiperazin-1-yl)methylbenzonitrile;
4-(1-(pyrrolidin-1-yl)propyl-2-yl)amino-2-(4-p-methoxyphenylpiperazin-1-yl)methylbenzonitrile; or
4-(N,N',N'-trimethyl-1,2-ethylenediamin-1-yl)-2-(4-trifluoromethoxyphenylpiperazin-1-yl)methylbenzonitrile.

7. The compound as claimed in claim 1, being a compound having the structure shown in the general formula VII or a pharmaceutically acceptable salt thereof:

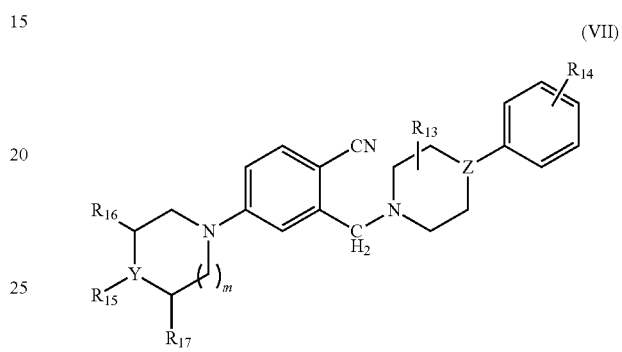

(VII)

wherein $R_{13}$ is H or C1-C4 alkyl, $R_{14}$ is H or one or more substituents selected from a group consisting of straight-chain or branched-chain C1-C4 alkyl, C5-C6 cycloalkyl, C1-C4 alkoxy, phenoxy, phenylthio, methylthio, amino, methylamino, dimethylamino, hydroxy, trifluoromethyl, trifluoromethoxy, cyano and halogen at any available position(s) of the phenyl ring, $R_{15}$ is H, C1-C4 alkyl, C2-C4 alkenyl, phenyl, amino, methylamino or dimethylamino, $R_{16}$ and $R_{17}$ are H, C1-C4 alkyl or amino respectively or simultaneously, Y is N or C, and $R_{15}$ is not amino, methylamino or dimethylamino simultaneously when Y is N, m is 0 or 1, and Y is C when m is 0.

8. The compound as claimed in claim 1, being a compound having the following structure as shown in Formula VIII or a pharmaceutically acceptable salt thereof:

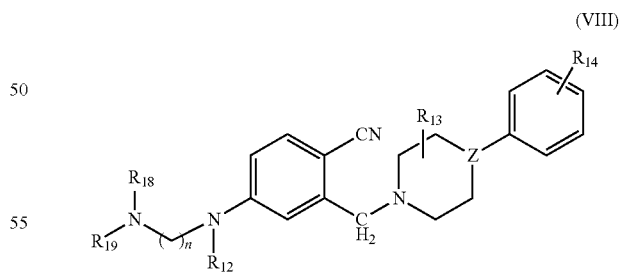

(VIII)

wherein, $R_{12}$ is H or C1-C4 alkyl, $R_{18}$ and $R_{19}$ are H or C1-C4 alkyl, or, form a saturated five- or six-membered ring together with the nitrogen atom to which they are bonded, the said saturated five- or six-membered ring is selected from a group consisting of pyrrolidine, morpholine, piperazine and piperidine, $R_{13}$ is H or C1-C4 alkyl, $R_{14}$ is H or one or more substituents selected from a group consisting of straight-chain or branched-chain C1-C4 alkyl, C5-C6 cycloalkyl, C1-C4 alkoxy, phenoxy, phenylthio, trifluoromethyl, trifluoromethoxy, and halogen at any available position(s) of the phenyl ring, n is an integer of 1-4, Z is N or C.

9. The compound as claimed in claim 1, being a compound having the structure shown in the general formula IX or a pharmaceutically acceptable salt thereof:

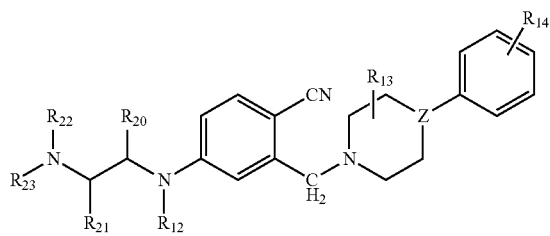

(IX)

wherein, $R_{23}$ is H or C1-C4 alkyl, $R_{22}$ and $R_{21}$ are H or C1-C4 alkyl, or $R_{22}$ and $R_{21}$ form a saturated five- or six-membered ring together with the nitrogen atoms to which they are bonded, the said saturated five- or six-membered ring is selected from a group consisting of pyrrolidine, morpholine, piperazine and piperidine, $R_{20}$ is H or C1-C4 alkyl, $R_{12}$ is H or C1-C4 alkyl, $R_{13}$ is H or C1-C4 alkyl, $R_{14}$ is H or one or more substituents selected from a group consisting of straight-chain or branched-chain C1-C4 alkyl, C5-C6 cycloalkyl, C1-C4 alkoxy, phenoxy, phenylthio and halogen at any available position(s) of the phenyl ring, Z is N or C.

10. The method for preparing the compound as claimed in claim 1, with 2-methyl-4-fluorobenzonitrile (A) as starting material, comprising:

a) obtaining intermediate compound (B) with methyl at position 2 monosubstituted by bromo via bromination by NBS, b) reacting the bromosubstituted intermediate then with the corresponding piperazine or piperidine substituted by aryl group, using sodium ethoxide or potassium carbonate as acid binding agent to obtain the corresponding intermediate compound (C), c) finally, condensing the intermediate compound (C) with the corresponding nitrogen-containing compound to remove HF, thereby obtaining the desired product (compound of formula VI) in the presence of a base in a polar solvent

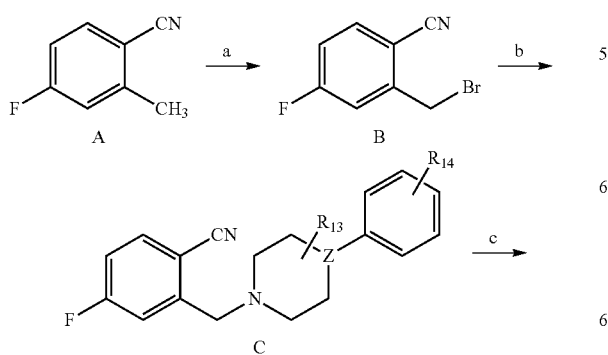

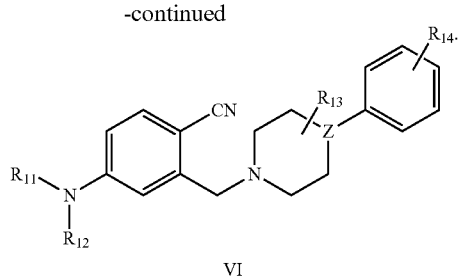

VI

11. An antiviral pharmaceutical composition comprising a therapeutically effective amount of a compound or a pharmaceutically acceptable salt thereof as claimed in claim 1, and comprising one or more pharmaceutically acceptable pharmaceutical auxiliary material, adjuvants or excipients.

12. The pharmaceutical composition as claimed in claim 1, wherein the pharmaceutically acceptable salt refers to the product from salt forming reaction of a compound as claimed with an acid, including inorganic acid salts and organic acid salts.

13. The method for preparing the compound as claimed in claim 1, with 2-methyl-4-fluorobenzonitrile or 6-fluoro-2-methyl-3-cyanopyridine (A) as a raw material, comprising:

a) obtaining intermediate (B) with methyl at position 2 monosubstituted by bromo via bromination by NBS, b) reacting the bromosubstituted intermediate then with the corresponding substituted aniline, using sodium ethoxide or potassium carbonate as acid binding agent to obtain the corresponding intermediate (C) of benzonitrile or cyanopyridine substituted by substituted phenylaminomethyl, c) finally, condensing the corresponding nitrogen-ccondensing the intermediate (C) with the corresponding nitrogen-containing compound to remove HF, thereby obtaining the desired product (compound of formula I) in the presence of a base in a polar solvent

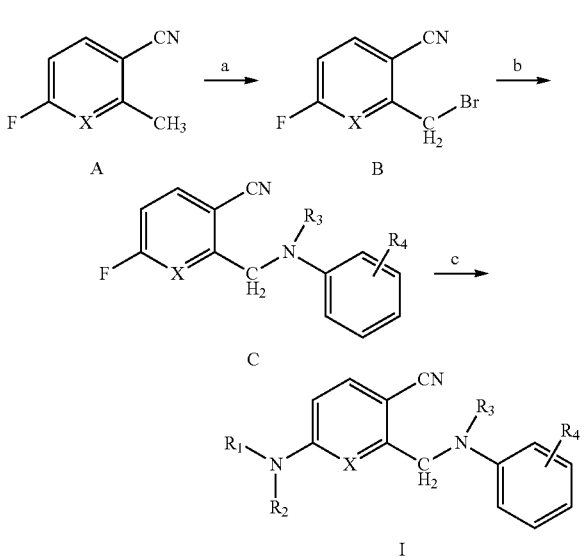

wherein, $R_1$, $R_2$, $R_3$, $R_4$, X are as claimed.

14. A method for treatment of viral diseases, wherein the viral diseases are caused by hepatitis C virus, DNA viruses, RNA virus, and the method comprises administering therapeutically effective amount of the compound as claimed in claim 1.

15. The compound as claimed in claim 1, wherein the substituents of $R_{14}$ are para-monosubstituted or are disubstituted at any position(s) of the phenyl ring.

16. The compound as claimed in claim 2, wherein $R_3$ is H, methyl, ethyl or propyl, $R_4$ is H or methyl, ethyl, isopropyl, tert-butyl, cyclopentyl, cyclohexyl, methoxy, ethoxy, phenoxy, phenylthio, chloro and bromo at para position of the phenyl ring, $R_5$ is H, methyl, ethyl, propyl, allyl or phenyl, $R_6$ and $R_7$ are H, methyl, ethyl, propyl or amino simultaneously or separately, Y is N or C.

17. The compound as claimed in claim 3, wherein $R_2$ is H, methyl or ethyl, $R_8$ and $R_9$ are H, methyl or ethyl, or, form a piperidine ring together with the nitrogen atom to which they are bonded, $R_3$ is H, methyl, ethyl or propyl, $R_4$ is H or methyl, ethyl, isopropyl, tert-butyl, methoxy, ethoxy, chloro or bromo at para position on the phenyl ring, n is 1, 2 or 3.

18. The compound as claimed in claim 4, wherein $R_3$ is H, methyl, ethyl or propyl, $R_4$ is H or methyl, ethyl, isopropyl, tert-butyl, cyclopentyl, cyclohexyl, methoxy, ethoxy, phenoxy, phenylthio, chloro or bromo at para position of the phenyl ring, $R_5$ is H, methyl, ethyl, propyl, allyl or phenyl, $R_6$ and $R_7$ are H, methyl, ethyl, propyl or amino simultaneously or separately, Y is N or C.

19. The compound as claimed in claim 5, wherein $R_2$ is H, methyl or ethyl, $R_8$ and $R_9$ are H, methyl or ethyl, or, form a piperidine ring together with the nitrogen atom to which they are bonded, $R_3$ is H, methyl, ethyl or propyl, $R_4$ is H or methyl, ethyl, isopropyl, tert-butyl, methoxy, ethoxy, chloro or bromo at para or meta position of the phenyl ring, n is 1, 2 or 3.

20. The compound as claimed in claim 7, wherein $R_{13}$ is H, methyl, ethyl or propyl, $R_{14}$ is H or the substitute(s) selected from a group consisting of methyl, ethyl, isopropyl, tert-butyl, cyclopentyl, cyclohexyl, methoxy, ethoxy, phenoxy, phenylthio, methylthio, amino, methylamino, dimethylamino, hydroxy, trifluoromethyl, trifluoromethoxy, cyano, chloro and bromo which is para-monosubstituted or are disubstituted at any positions of the phenyl ring, $R_{15}$ is H, methyl, ethyl, propyl, allyl or phenyl, $R_{16}$ and $R_{17}$ are H, methyl, ethyl, propyl, or amino respectively or simultaneously, Y is N or C; $R_{15}$ are not amino, methylamino or dimethylamino simultaneously when Y is N; m is 0 or 1; and Y is C when m is 0.

21. The compound as claimed in claim 8, wherein $R_{12}$ is H, methyl or ethyl, $R_{18}$ and $R_{19}$ are H, methyl or ethyl, or, form a pyrrolidine or piperidine ring together with the nitrogen atom to which they are bonded, $R_{13}$ is H, methyl, ethyl or propyl, $R_{14}$ is H, or the substitute(s) selected from a group consisting of methyl, ethyl, isopropyl, tert-butyl, methoxy, ethoxy, trifluoromethyl, trifluoromethoxy, chloro and bromo which is para-monosubstituted or are disubstituted at any positions of the phenyl ring, n is 1, 2, 3, Z is N or C.

22. The compound as claimed in claim 9, wherein $R_{23}$ is H, methyl or ethyl, $R_{22}$ and $R_{21}$ are H, methyl or ethyl, or $R_{22}$ and $R_{21}$ form a pyrrolidine or piperidine ring together with the nitrogen atom to which they are bonded, $R_{20}$ is H, methyl or ethyl, $R_{12}$ is H, methyl or ethyl, $R_{13}$ is H, methyl, ethyl or propyl, $R_{14}$ is H, or substitute(s) selected from a group consisting of methyl, ethyl, isopropyl, tert-butyl, methoxy, ethoxy, chloro and bromo which is para-monosubstituted or are disubstituted at any positions of the phenyl ring, Z is N or C.

23. The pharmaceutical composition as claimed in claim 12, wherein the inorganic acid salts is hydrochloride, hydrobromide or sulfate, and wherein the organic acid salts is acetate, lactate, succinate, fumarate, maleate, citrate, benzoate, methanesulfonate, or 4-methylbenzoate salt.

* * * * *